(12) United States Patent
Cox et al.

(10) Patent No.: US 10,238,630 B2
(45) Date of Patent: Mar. 26, 2019

(54) USE OF ERIBULIN AND POLY (ADP RIBOSE) POLYMERASE (PARP) INHIBITORS AS COMBINATION THERAPY FOR THE TREATMENT OF CANCER

(71) Applicant: Eisai R&D Management Co., Ltd., Tokyo (JP)

(72) Inventors: David Cox, Oakland, NJ (US); Alton Kremer, Weston, CT (US); Sharon McGonigle, Andover, MA (US); Jiayi Wu, Brookline, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 26 days.

(21) Appl. No.: 15/314,200

(22) PCT Filed: May 28, 2015

(86) PCT No.: PCT/US2015/032990
§ 371 (c)(1),
(2) Date: Nov. 28, 2016

(87) PCT Pub. No.: WO2015/184145
PCT Pub. Date: Dec. 3, 2015

(65) Prior Publication Data
US 2017/0100368 A1    Apr. 13, 2017

Related U.S. Application Data

(60) Provisional application No. 62/088,200, filed on Dec. 5, 2014, provisional application No. 62/003,798, filed on May 28, 2014.

(51) Int. Cl.
*A61K 31/357*    (2006.01)
*A61K 31/555*    (2006.01)
*A61K 31/519*    (2006.01)
*A61K 45/06*    (2006.01)

(52) U.S. Cl.
CPC .......... *A61K 31/357* (2013.01); *A61K 31/519* (2013.01); *A61K 31/555* (2013.01); *A61K 45/06* (2013.01)

(58) Field of Classification Search
CPC .. A61K 31/357; A61K 31/519; A61K 31/555; A61K 45/06
USPC ....................................................... 514/248
See application file for complete search history.

(56) References Cited

U.S. PATENT DOCUMENTS 6,653,341 B1    11/2003    Littlefield et al.
8,236,802 B2    8/2012    Xu et al.

FOREIGN PATENT DOCUMENTS

| WO | WO-2009/046205 A1 | 4/2009 |
|---|---|---|
| WO | WO-2012/129100 A1 | 9/2012 |
| WO | WO-2013/066440 A1 | 5/2013 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Hashimoto et al., "Synergistic interaction betweem olaparib, a parp inhibitor, and cytotoxic agent in triple negative breast cancer," Annals of Oncology. 24(Supplement 9):ix31-ix65 (2013) (Abstract).
International Search Report and Written Opinion dated Aug. 14, 2015, for International Application No. PCT/US2015/032990, Cox et al., "Use of Eribulin and Poly (ADP Ribose) Polymerase (PARP) Inhibitors as Combination Therapy for the Treatment of Cancer," filed May 28, 2015, (19 pages).
Kaklamani et al., "Abstract OT2-2-02: phase I/II clinical trial on the combination of carboplatin, eribulin and E7449," Proceedings of the Thirty-Seventh Annual CTRC-AACR San Antonio Breast Cancer Symposium: Dec. 9-13, 2014, San Antonio, TX. Cancer Res. 75(9 Suppl):Abstract No. OT2-2-02 (2015).
Schööffski et al., "Activity of eribulin mesylate in patients with soft-tissue sarcoma: a phase 2 study in four independent histological subtypes," Lancet Oncol. 12(11):1045-52 (2011). Abstract.
Anonymous, "Olaprib Phase I/II clinical trial in combination with eribulin for operable/recurrent breast cancer of triple negative type with treatment history of anthracycline and taxane drugs," 2012 <https://upload.umin.ac.jp/cgi-open-bin/ctr/ctr.cgi?function=brows&action=brows&type=summary&recptno=R000011159&language=J> retrieved Oct. 31, 2014 (11 pages).
Extended European Search Report dated Nov. 10, 2017 for European Patent Application No. 15799685.1, Cox et al., "Use of eribulin and poly (ADP ribose) polymerase (PARP) inhibitors as combination therapy for the treatment of cancer," filed May 28, 2015 (9 pages).

* cited by examiner

*Primary Examiner* — Kristin A Vajda
(74) *Attorney, Agent, or Firm* — Clark & Elbing LLP; Susan M. Michaud

(57) ABSTRACT

The invention features methods for treating cancer in a patient in need thereof by administering eribulin, in combination with one or more PARP inhibitors, and, optionally, a platinum-based antineoplastic drug, and kits therefor. The invention is based in part on the observation that combinations of eribulin mesylate, a PARP inhibitor (e.g., E7449), and, optionally, a platinum-based antineo-plastic drug (e.g., carboplatin), show improved (e.g., synergistic) antitumor effects. Therefore, the present invention features methods of preventing and treating cancer (e.g., homologous recombination (HR)-deficient cancer by the use of combinations of eribulin (e.g., eribulin mesylate) and one or more PARP inhibitors (e.g., E7449 or a pharmaceutically acceptable salt thereof (e.g., the tartrate salt), optionally in combination with a platinum-based antineoplastic drug (e.g., carboplatin).

27 Claims, 17 Drawing Sheets

USE OF ERIBULIN AND POLY (ADP RIBOSE) POLYMERASE (PARP) INHIBITORS AS COMBINATION THERAPY FOR THE TREATMENT OF CANCER

BACKGROUND OF THE INVENTION

Cancer is a term used to describe a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine with certainty the extent of metastasis, systemic approaches to therapy are usually undertaken when any evidence of spread is detected. These approaches involve the administration of, for example, chemotherapeutic drugs that interfere with the growth of rapidly dividing cells, such as cancer cells. Other approaches involve the use of immunotherapy, in which an immune response against cancerous cells in a subject is elicited or enhanced.

Halichondrin B is a structurally complex, macrocyclic compound that was originally isolated from the marine sponge *Halichondria okadai*, and subsequently was found in *Axinella* sp., *Phakellia carteri*, and *Lissodendoryx* sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, beta$^S$-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

Eribulin is a synthetic analog of halichondrin B. Eribulin is also known as ER-086526, and has been assigned CAS number 253128-41-5 and US NCI designation number NSC-707389. The mesylate salt of eribulin (eribulin mesylate, which is marketed under the trade name HALAVEN® and is also known as E7389) received FDA approval in November of 2010 for the treatment of patients with metastatic breast cancer who have previously received at least two chemotherapeutic regimens for the treatment of metastatic disease that should have included an anthracycline and a taxane in either the adjuvant or metastatic setting.

The chemical name for eribulin mesylate is 11, 15:18,21: 24,28-triepoxy-7,9-ethano-12,15-methano-9H,15H-furo[3,2-i]furo[2',3':5,6]pyrano[4,3-b] [1,4]dioxacyclopentacosin-5(4H)-one, 2-[(2S)-3-amino-2-hydroxypropyl] hexacosahydro-3-methoxy-26-methyl-20,27-bis (methylene)-, (2R,3R,3aS,7R,8aS,9S,10aR,11S,12R,13aR, 13bS,15S,18S,21S,24S,26R,28R,29aS)-methanesulfonate (salt), and it may be depicted as follows:

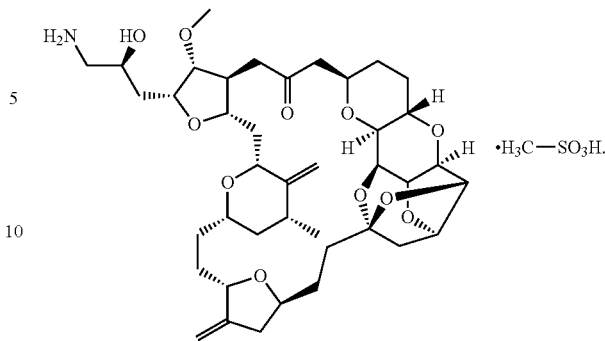

Members of the poly (ADP-ribose) polymerase (PARP) family of proteins are involved in a number of cellular processes involving mainly DNA repair and programmed cell death. PARP inhibitors are under development for a number of indications including cancer. E7449 is a PARP inhibitor (see compound 37 in U.S. Pat. No. 8,236,802), and may be depicted as follows:

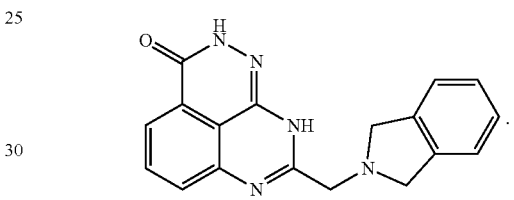

SUMMARY OF THE INVENTION

The invention is based in part on the observation that combinations of eribulin mesylate, a PARP inhibitor (e.g., E7449), and, optionally, a platinum-based antineoplastic drug (e.g., carboplatin), show improved (e.g., synergistic) antitumor effects. Therefore, the present invention features methods of preventing and treating cancer (e.g., homologous recombination (HR)-deficient cancer; see below) by the use of combinations of eribulin (e.g., eribulin mesylate) and one or more PARP inhibitors (e.g., E7449 or a pharmaceutically acceptable salt thereof (e.g., the tartrate salt), optionally in combination with a platinum-based antineoplastic drug (e.g., carboplatin).

When the term "eribulin" is used herein, it should be considered as indicating eribulin or a pharmaceutically acceptable salt thereof (such as eribulin mesylate), unless the context indicates otherwise. Similarly, when the term "PARP inhibitor" (or the name of a specific PARP inhibitor, such as E7449) is used herein, it should be considered as indicating the PARP inhibitor or a pharmaceutically acceptable salt (e.g., the L-tartrate salt), hydrate, solvate, or amorphous solid thereof, as applicable, unless the context indicates otherwise.

In a first aspect, the invention provides methods for treating a subject (e.g., a human patient) having or at risk of developing cancer (e.g., a subject diagnosed with a cancer, in treatment for cancer, or in post-therapy recovery from cancer). The methods include administering to the subject (i) eribulin or a pharmaceutically acceptable salt thereof (e.g., eribulin mesylate), and (ii) a poly (ADP-ribose) polymerase (PARP) inhibitor, or a pharmaceutically acceptable salt, hydrate, solvate, or amorphous solid thereof.

In various embodiments, the cancer is homologous recombination (HR)-deficient. For example, the HR-deficient cancer may be BRCA1, BRCA2, PTEN, ATM, MRE11, PALB2, RAD54, RAD54B, RAD50, RAD51, RAD51B, RAD51C, RAD51D, DMC1, XRCC2, SRCC3, RAD52, BRIP1, NBS1, WRN, BLM, Ku70, Ku80, ATR chk1, chk2, FANCA, FANCB, FANCC, FANCD1, FANCD2, FANCE, FANCF, FANCG, RAD1, RAD9, FEN-1, Mus81, Eme1, DDS1, BARD, XRCC1, ADPRT (PARP-1), ADPRTL2 (PARP-2), CTPS, RPA, RPA1, RPA2, RPA3, XPD, ERCC1, XPF, and/or MMS19 deficient.

In some embodiments, the cancer is a primary tumor, a metastasis, and/or a solid tumor.

In certain embodiments, the cancer is selected from the group consisting of breast cancer (e.g., estrogen receptor positive or negative, progesterone receptor positive or negative, HER-2 positive or negative, triple-negative breast cancer, or BRCA1 and/or BRCA2 positive or negative), lung cancer (e.g., non-small cell lung cancer and small cell lung cancer), ovarian cancer, endometrial cancer, prostate cancer, pharyngeal cancer, esophageal cancer, glioblastoma, adrenal cancer, B-cell malignancies, biliary tract cancer, bladder cancer, bone cancer, brain cancer, cervical cancer, choriocarcinoma, colon cancer, colorectal cancer, connective tissue cancer, cancer of the digestive system, gallbladder cancer, gastric cancer, cancer of the head and neck, hepatocellular carcinoma, intra-epithelial neoplasm, kidney cancer, liver cancer, lymphoma, skin cancer (e.g., melanoma and basal cell carcinoma), neuroblastoma, mesothelioma, neuroglioma, oral cavity cancer, pediatric cancer, pancreatic cancer, pancreatic endocrine tumors, pituitary adenoma, thymoma, renal cell carcinoma, cancer of the respiratory system, salivary gland cancer, sarcoma (e.g., Ewing's sarcoma, fibrosarcoma, and rhabdomyosarcoma), small bowel cancer, testicular cancer, thyroid cancer, ureteral cancer, cancer of the urinary system, and hematological cancers (e.g., acute myeloid leukemia and multiple myeloma).

In various embodiments, the eribulin or the pharmaceutically acceptable salt thereof is administered by intravenous infusion for, e.g., about 1 to about 20 minutes, or about 2 to about 5 minutes, in an amount in the range of about 0.1 $mg/m^2$ to about 20 $mg/m^2$, or in an amount of about 0.7 $mg/m^2$, 1.1 $mg/m^2$, or 1.4 $mg/m^2$. The administration can take place, for example, once on each of days 1 and 8 of a 21-day cycle.

In some embodiments, the PARP inhibitor is selected from the group consisting of E7449, olaparib, niraparib, rucaparib, veliparib, and BMN 673, and pharmaceutically acceptable salts, hydrates, solvates, or amorphous solid thereof. In specific examples, the PARP inhibitor is E7449 or a pharmaceutically acceptable salt thereof (e.g., the L-tartrate salt), and can optionally be administered orally, e.g., in an amount in the range of about 100 mg to about 1000 mg, or in an amount of about 200, 400, 600, or 800 mg. The administration can take place, for example, once daily during a 21-day cycle.

In certain embodiments, the methods further include administration of a platinum-based antineoplastic drug (e.g., cisplatin, carboplatin, oxaliplatin, satraplatin, picoplatin, nedaplatin, triplatin, or lipolatin), which optionally can be administered once during a 21-day cycle.

In various embodiments, treatment according to the methods of the invention: (i) reduces the number of cancer cells; (ii) reduces tumor volume; (iii) increases tumor regression rate; (iv) reduces or slows cancer cell infiltration into peripheral organs; (v) reduces or slows tumor metastasis; (vi) reduces or inhibits tumor growth; (vii) prevents or delays occurrence and/or recurrence of the cancer and/or extends disease- or tumor-free survival time; (viii) increases overall survival time; (ix) reduces the frequency of treatment; and/or (x) relieves one or more of symptoms associated with the cancer.

In another aspect, the invention provides methods for decreasing the size of a tumor (e.g., a tumor including HR-deficient cells; see above) in a subject (e.g., a human patient). The methods involve administering to the subject (i) eribulin or a pharmaceutically acceptable salt thereof (e.g., eribulin mesylate), and (ii) a PARP inhibitor or a pharmaceutically acceptable salt, hydrate, solvate, or amorphous solid thereof (e.g., E7449 or a pharmaceutically acceptable salt thereof, such as the L-tartrate salt; also see above). Optionally, these methods further include administration of a platinum-based antineoplastic drug (see above).

In any of the methods and embodiments described above, the amount of the eribulin, or the pharmaceutically acceptable salt thereof (e.g., eribulin mesylate), and/or the amount of the PARP inhibitor or the pharmaceutically acceptable salt, hydrate, solvate, or amorphous solid thereof (e.g., the L-tartrate salt of E7449) administered to the subject provides a synergistic effect greater than the sum of the individual effects.

In methods including administration of a platinum-based antineoplastic drug, the amount of the eribulin, or the pharmaceutically acceptable salt thereof (e.g., eribulin mesylate), the amount of the PARP inhibitor or the pharmaceutically acceptable salt, hydrate, solvate, or amorphous solid thereof (e.g., the L-tartrate salt of E7449), and/or the amount of the platinum-based antineoplastic drug administered to the subject provides a synergistic effect greater than the sum of the individual effects.

In any of the methods and embodiments described above, the eribulin, or the pharmaceutically acceptable salt thereof (e.g., eribulin mesylate), or the PARP inhibitor, or the pharmaceutically acceptable salt, hydrate, solvate, or amorphous solid thereof (e.g., the L-tartrate salt of E7449), may be co-administered.

In any of the methods and embodiments described above, the eribulin, or the pharmaceutically acceptable salt thereof (e.g., eribulin mesylate), or the PARP inhibitor, or the pharmaceutically acceptable salt, hydrate, solvate, or amorphous solid thereof (e.g., the L-tartrate salt of E7449), may be administered sequentially.

The co-administration and sequential administration methods noted above may optionally further include co-administration of a platinum-based antineoplastic drug with either or both of the eribulin, or the pharmaceutically acceptable salt thereof (e.g., eribulin mesylate), or the PARP inhibitor, or the pharmaceutically acceptable salt, hydrate, solvate, or amorphous solid thereof (e.g., the L-tartrate salt of E7449), or further include sequential administration of a platinum-based antineoplastic drug relative to the eribulin, or the pharmaceutically acceptable salt thereof (e.g., eribulin mesylate), or the PARP inhibitor, or the pharmaceutically acceptable salt, hydrate, solvate, or amorphous solid thereof (e.g., the L-tartrate salt of E7449).

In another aspect, the invention provides kits for use in treating cancer or decreasing tumor size (see, e.g., the cancer and tumor types listed above and elsewhere herein). The kits may include (i) eribulin or a pharmaceutically acceptable salt thereof (e.g., eribulin mesylate), and (ii) a PARP inhibitor or a pharmaceutically acceptable salt, hydrate, solvate, or amorphous solid thereof (e.g., E7449 or a pharmaceutically acceptable salt thereof, such as the L-tartrate salt). Optionally, the kits may also include a platinum-based antineoplastic drug (e.g., cisplatin, carboplatin, oxaliplatin, satraplatin, picoplatin, nedaplatin, triplatin, and/or lipolatin).

The invention further includes the use of (i) eribulin or a pharmaceutically acceptable salt thereof (e.g., eribulin mesylate), and (ii) a PARP inhibitor or a pharmaceutically acceptable salt, hydrate, solvate, or amorphous solid thereof (e.g., E7449 or a pharmaceutically acceptable salt thereof, such as the L-tartrate salt, or other PARP inhibitors, such as one or more of those described herein) for treating cancer or decreasing tumor size (see, e.g., the cancer and tumor types listed herein), or for preparing a medicament for this purpose. Optionally, these uses can also include use of one or more platinum-based antineoplastic drugs (e.g., cisplatin, carboplatin, oxaliplatin, satraplatin, picoplatin, nedaplatin, triplatin, and/or lipolatin), as described herein.

Other features and advantages of the invention will be apparent from the following detailed description, drawings, and claims.

DETAILED DESCRIPTION OF THE INVENTION

Figure 1:
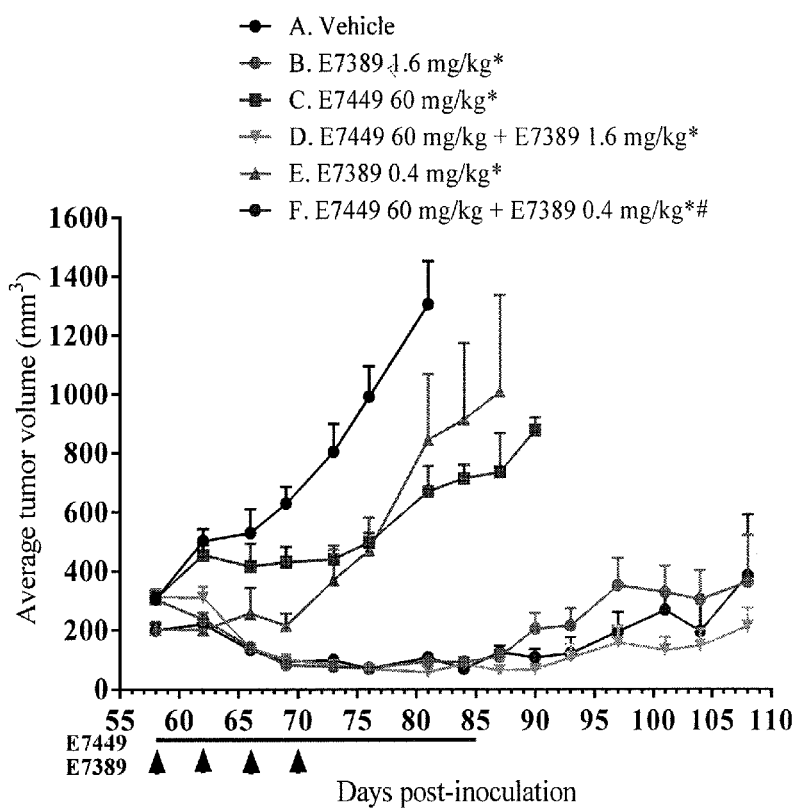
FIG. 1 is a graph showing an antitumor effect of E7449 and E7389 (eribulin mesylate) alone and in combination in MDA-MB-436 human breast cancer xenografts in SCID Mice. Average tumor volume for the indicated treatment groups is shown as a function of time post inoculation.

The invention provides methods for the treatment of cancer involving administration of eribulin or a pharmaceutically acceptable salt thereof (e.g., eribulin mesylate) and one or more PARP inhibitors (e.g., E7449 or a pharmaceutically acceptable salt thereof (e.g., the L-tartrate salt)), optionally in combination with a platinum-based antineoplastic drug (e.g., carboplatin). Cancer that may be treated according to the invention includes, for example, homologous recombination (HR)-deficient cancer, as described further below.

Treatment of cancer by administering eribulin or a pharmaceutically acceptable salt thereof (e.g., eribulin mesylate), a PARP inhibitor (e.g., E7449 or a pharmaceutically acceptable salt thereof (e.g., the L-tartrate salt)), optionally in combination with a platinum-based antineoplastic drug (e.g., carboplatin), according to the methods of the invention, may (i) reduce the number of cancer cells; (ii) reduce tumor volume; (iii) increase tumor regression rate; (iv) reduce or slow cancer cell infiltration into peripheral organs; (v) reduce or slow tumor metastasis; (vi) reduce or inhibit tumor growth; (vii) prevent or delay occurrence and/or recurrence of the cancer and/or extend disease- or tumor-free survival time; (viii) increase overall survival time; (ix) reduce the frequency of treatment; and/or (x) relieve one or more of symptoms associated with the cancer. The skilled artisan appreciates that treatment of cancer may result in patient health improvement even though the cancer is not cured or entirely removed.

Pharmaceutical Compositions, Dosage, and Methods

Methods for the synthesis of eribulin are described, for example, in U.S. Pat. No. 6,214,865; U.S. Pat. No. 7,982,060; U.S. Pat. No. 8,350,067; and U.S. Pat. No. 8,093,410, each of which is incorporated herein by reference. As noted above, eribulin mesylate is available commercially and is marketed as HALAVEN®. Methods relating to E7449 and its synthesis are described, for example, in U.S. Pat. No. 8,236,802, which is incorporated herein by reference. As discussed further below, PARP inhibitors in addition to E7449 may also be used in the invention and are available commercially or may be synthesized using methods known in the art. Platinum-based antineoplastic drugs (e.g., carboplatin) are well known in the art and available commercially (see below).

As noted above, eribulin and/or PARP inhibitors may optionally be used in the present invention in a salt form. There are no particular limitations as to the salt used, whether inorganic acid salt or organic acid salt. For example, the salt may be selected from mesylic acid salt (e.g., eribulin mesylate), hydrochloric acid salt, sulfuric acid salt, citrate, hydrobromic acid salt, hydroiodine acid salt, nitric acid salt, bisulfate, phosphoric acid salt, super phosphoric acid salt, isonicotinic acid salt, acetic acid salt, lactic acid salt, salicic acid salt, tartaric acid salt, L-tartrate salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate), and so on. Moreover, it is acceptable to use a salt of aluminum, calcium, lithium, magnesium, sodium, zinc, or diethanolamine.

Pharmaceutical compositions including eribulin (or a pharmaceutically acceptable salt thereof (e.g., eribulin mesylate)), a PARP inhibitor (e.g., E7449 or a pharmaceutically acceptable salt thereof (e.g., the L-tartrate salt)), and a platinum-based antineoplastic drug (carboplatin), may be prepared using standard methods known in the art (see, e.g., the patent documents noted above). Typically, these drugs as used in the invention are included within separate pharmaceutical compositions but they can, optionally, be included within a single composition. Eribulin (e.g., eribulin mesylate) and platinum-based antineoplastic drugs (e.g., carboplatin) are typically provided or reconstituted in liquid form, for intravenous administration, while PARP inhibitors (e.g., E7449 or a pharmaceutically acceptable salt thereof (e.g., the L-tartrate salt)), in many instances, are typically provided in capsule form, for oral administration.

Pharmaceutical compositions used in the invention may be prepared by, for example, mixing or dissolving the active ingredient(s), having the desired degree of purity, in a physiologically acceptable diluent, carrier, excipient, or stabilizer (see, e.g., Remington's Pharmaceutical Sciences (20$^{th}$ edition), ed. A. Gennaro, 2000, Lippincott, Williams & Wilkins, Philadelphia, Pa.). Acceptable diluents include water and saline, optionally including buffers such as phosphate, citrate, or other organic acids; antioxidants including butylated hydroxytoluene (BHT), butylated hydroxyanisole (BHA), ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, or other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

In preparing compositions for oral dosage form (e.g., compositions including a PARP inhibitor, such as E7449 or a pharmaceutically acceptable salt thereof (e.g., the L-tartrate salt)), any of the usual pharmaceutical media may be employed, for example, water, glycols, oils, alcohols, flavoring agents, preservatives, coloring agents. In addition, carriers such as starches, sugars, microcrystalline cellulose, diluents, granulating agents, lubricants, binders, disintegrating agents, and the like may be used in the case of oral solid preparations such as, for example, powders, capsules, and tablets.

Optionally, the formulations of the invention may contain a pharmaceutically acceptable preservative. In some embodiments the preservative concentration ranges from 0.1 to 2.0%, typically v/v. Suitable preservatives include those known in the pharmaceutical arts, such as benzyl alcohol, phenol, m-cresol, methylparaben, and propylparaben. Further, the eribulin and/or PARP inhibitor formulations may optionally include a pharmaceutically acceptable salt, such as sodium chloride at, for example, about physiological concentrations. Thus, in one example, eribulin is formulated in 0.9% Sodium Chloride Injection (USP).

The formulations noted above (and others) may be used for parenteral administration of the drugs. Thus, the drugs may be administered by routes including intravenous, intratumoral, peri-tumoral, intra-arterial, intra-dermal, intra-vesical, ophthalmic, intramuscular, intradermal, intraperitoneal, pulmonary, subcutaneous, and transcutaneous routes. Other routes may also be used including, for example, transmucosal, transdermal, inhalation, intravaginal, rectal, and oral administration routes.

The dosage of the eribulin (e.g., eribulin mesylate), PARP inhibitor (e.g., E7449 or a pharmaceutically acceptable salt thereof (e.g., the L-tartrate salt)), and platinum-based antineoplastic drug (e.g., carboplatin) compositions administered may differ markedly depending on the type of target disease, the choice of delivery method, as well as the age, sex, and weight of the patient, the severity of the symptoms, along with other factors. Furthermore, eribulin (e.g., eribulin mesylate), PARP inhibitor (e.g., E7449 or a pharmaceutically acceptable salt thereof (e.g., the L-tartrate salt)), and, optionally, platinum-based antineoplastic drug (e.g., carboplatin) compositions may be administered to a patient substantially simultaneously or sequentially, and in any order.

The daily dosage of eribulin (e.g., eribulin mesylate) may be in the range of, e.g., 0.001 mg/m$^2$ to about 100 mg/m$^2$ (e.g., in the range of about 0.1 mg/m$^2$ to about 50 mg/m$^2$ or in the range of about 0.7 mg/m$^2$ to about 1.5 mg/m$^2$, or in any single amount within these ranges (e.g., 1.4 mg/m$^2$ or 1.1 mg/m$^2$)). Eribulin (e.g., eribulin mesylate) may be administered as a single dose once a day, week, month, or year, or more than one dose may be administered per day, week, month, or year. For example, in one administration protocol, eribulin (e.g., eribulin mesylate) may be administered once on days 1 and 8 of a 21-day cycle. More specifically, a recommended dose of eribulin (e.g., eribulin mesylate) is 1.4 mg/m$^2$ administered intravenously over 2 to 5 minutes on days 1 and 8 of a 21-day cycle. A recommended dose of eribulin (e.g., eribulin mesylate) in patients with mild hepatic impairment (Child-Pugh A) is 1.1 mg/m$^2$ administered intravenously over 2 to 5 minutes on days 1 and 8 of a 21-day cycle, while a recommended dose of eribulin (e.g., eribulin mesylate) in patients with moderate hepatic impairment (Child-Pugh B) is 0.7 mg/m² administered intravenously over 2 to 5 minutes on days 1 and 8 of a 21-day cycle. Further, a recommended dose of eribulin (e.g., eribulin mesylate) in patients with moderate renal impairment (creatinine clearance of 30-50 mL/min) is 1.1 mg/m² administered intravenously over 2 to 5 minutes on days 1 and 8 of a 21-day cycle. These or other lower doses of eribulin (e.g., eribulin mesylate) may optionally be used in the context of combination treatment, according to the methods of the present invention. In particular examples, when eribulin is administered in combination with other agents, as described herein, the dose may be reduced from 1.4 mg/m² administered intravenously over 2 to 5 minutes on days 1 and 8 of a 21-day cycle, to 1.1 mg/m² or 0.7 mg/m² administered intravenously over 2 to 5 minutes on days 1 and 8 of a 21-day cycle.

PARP inhibitors may be administered using regimens determined to be appropriate by those of skill in the art. E7449 (or a pharmaceutically acceptable salt thereof (e.g., the L-tartrate salt)), for example, may be orally administered in a range of about 10 mg/day to about 1000 mg/day (e.g., 10, 50, 100, 200, 400, 600, or 800 mg/day), in single or divided doses. In one embodiment, E7449 can be orally administered in a range of about 20 mg/day to about 400 mg/day. E7449 (or a pharmaceutically acceptable salt thereof (e.g., the L-tartrate salt)) may be administered as a single dose once a day, week, month, or year, or more than one dose of E7449 (or a pharmaceutically acceptable salt thereof (e.g., the L-tartrate salt)) may be administered per day, week, month, or year. In various examples, E7449 (or a pharmaceutically acceptable salt thereof (e.g., the L-tartrate salt)) may be administered in decreasing or increasing step doses, such that the second and subsequent doses administered are reduced or increased relative to the first, and preceding, dose.

As noted above, PARP inhibitors other than E7449 may also be used in the invention. Thus, for example, the invention includes the use of reversible nicotinamide-mimetic small molecule PARP inhibitors, such as, for example, olaparib (AstraZeneca), niraparib (Tesaro), rucaparib (Clovis Oncology), veliparib (AbbVie), and BMN 673 (BioMarin). Standard methods for administration of these drugs are known in the art and may be adapted for use in the present invention. In view of the combination therapy, standard amounts of these drugs may be used or may be reduced, as determined to be appropriate by those of skill in the art.

Platinum-based antineoplastic drugs (platins) that may be used in the invention include, for example, cisplatin, carboplatin, oxaliplatin, satraplatin, picoplatin, nedaplatin, triplatin, and lipolatin. Dosing and administration regimens for these drugs are well known in the art and may readily be adapted for use in the present invention. In various embodiments, the amount of platinum-based antineoplastic drug may be reduced, as compared to standard doses, in view of the co-administration of eribulin (e.g., eribulin mesylate) and PARP inhibitor (e.g., E7449 (or a pharmaceutically acceptable salt thereof (e.g., the L-tartrate salt)). In the case of carboplatin, for example, reference may be made to Calvert et al., J. Clin. Oncol. 7:1748-1756, 1989, which explains well known approaches to dose determination based on, for example, glomerular filtration rate. As specific examples, a platinum-based antineoplastic drug (e.g., carboplatin) may be administered in the amount of AUC 4/5/6 IV Q3 weeks.

Many regimens used to administer chemotherapeutic drugs involve, for example, a course of administration of a drug (or drugs) followed by repetition of this treatment, optionally after a period (e.g., 1-4 weeks) during which the patient recovers from any adverse side effects of the treatment, as may be determined to be appropriate by those of skill in the art.

As a specific, non-limiting example of a treatment regimen included in the invention, eribulin (e.g., eribulin mesylate) is administered in the amount of 0.01-5 mg/m² (e.g., 0.7 or 1.1 mg/m²) by intravenous infusion for 0.5-3 hours (e.g., 2-5 minutes) on days 1 and 8 of a 21 day cycle, while a PARP inhibitor such as E7449 (or a pharmaceutically acceptable salt thereof (e.g., the L-tartrate salt)) is orally administered on a daily basis in the amount of 100 mg to 1000 mg (e.g., 200, 400, 600, or 800 mg) during this 21 day cycle. Optionally, a platinum-based antineoplastic drug (e.g., carboplatin) is administered once during this 21 day cycle. This administration may take place on the first day of the cycle or at any day determined to be appropriate by those of skill in the art (e.g., on day 1, 2, 3, 4, 5, 6, 7, 8, 9, 10, 11, 12, 13, 14, 15, 16, 17, 18, 19, 20, and/or 21). This course of treatment may be repeated, as determined to be tolerable and effective by those of skill in the art.

In one embodiment, E7449 is administered in subjects orally once a day (e.g., 10, 50, 100, 200, or 400 mg/day) continuously in 21 day cycles in combination with carboplatin and eribulin mesylate both of which are administered via intravenous infusion only on day 1 of each cycle. The skilled artisan appreciates that subjects may have one or more such 21-day cycles of treatment during which disease progression in the subject is monitored. In one embodiment, subjects will have 1, 2, 3, 4, 5, or 6 such 21 day cycles.

In other examples, the following dosing schedules can be used: (i) Dose level 1: carboplatin AUC 4 IV q 21 days; eribulin 1.1 mg/m² IV day 1, day 8 of 21 day cycle; E7449 200 mg po qd×21 days; (ii) Dose level 2: carboplatin AUC 4 IV q 21 days; eribulin 1.1 mg/m² IV day 1, day 8 of 21 day cycle; E7449 400 mg po qd×21 days; (iii) Dose level 3: carboplatin AUC 4 IV q 21 days; eribulin 1.1 mg/m² IV day 1, day 8 of 21 day cycle; E7449 600 mg po qd×21 days; (iv) Dose level 4: carboplatin AUC 5 IV q 21 days; eribulin 1.1 mg/m² IV day 1, day 8 of 21 day cycle; E7449 600 mg po qd×21 days; (v) Dose level 5: carboplatin AUC 6 IV q 21 days; eribulin 1.1 mg/m² IV day 1, day 8 of 21 day cycle; E7449 600 mg po qd×21 days In addition to eribulin, a PARP inhibitor (e.g., E7449 (or a pharmaceutically acceptable salt thereof (e.g., the L-tartrate salt)), and, optionally, a platinum-based antineoplastic drug (e.g., carboplatin), the methods of the present invention may also include the administration of one or more additional therapeutic agents. Among these agents, immunomodulatory agents (e.g., antibodies or vaccines), chemotherapeutic/antitumor agents, antibacterial agents, antiemetics, and anti-inflammatory agents are suitable. Alternatively, eribulin, a PARP inhibitor (e.g., E7449 (or a pharmaceutically acceptable salt thereof (e.g., the L-tartrate salt)), and, optionally a platinum-based antineoplastic drug (e.g., carboplatin), may be used in a treatment regimen as the sole therapeutic (e.g., sole anti-cancer) agents.

The methods of the invention may be used to treat (including, e.g., delay progression) or prevent cancer in a subject (e.g., a human patient) and/or to decrease tumor size. The subject may be diagnosed with cancer, at risk for developing cancer, in treatment for cancer, or in post-therapy recovery from cancer. Further, the methods may be used to treat or prevent metastases and/or recurrence. The treatment may be chemotherapeutic alone, although treatment in combination with a surgical procedure to remove or reduce the size of a tumor, radiation therapy, immunotherapy, and/or ablation therapy is also envisioned.

The methods of the invention may be used to treat cancer, including as non-limiting examples homologous recombination (HR)-deficient cancers, which are cancers characterized by cancer cells that have a reduced ability to carry out homologous recombination. HR-deficient cancers may be caused by a defect in expression of a gene that plays a role in HR due to, e.g., mutation. Genes that may function in HR include, for example, BRCA1, BRCA2, PTEN, ATM, MRE11, PALB2, RAD54, RAD54B, RAD50, RAD51, RAD51B, RAD51C, RAD51D, DMC1, XRCC2, SRCC3, RAD52, BRIP1, NBS1, WRN, BLM, Ku70, Ku80, ATR chk1, chk2, FANCA, FANCB, FANCC, FANCD1, FANCD2, FANCE, FANCF, FANCG, RAD1, RAD9, FEN-1, Mus81, Eme1, DDS1, BARD, XRCC1, ADPRT (PARP-1), ADPRTL2 (PARP-2), CTPS, RPA, RPA1, RPA2, RPA3, XPD, ERCC1, XPF, and MMS19. Specific, non-limiting examples of cancer types that may be treated according to the methods of the invention include the following, which optionally may be characterized as being HR-deficient: breast cancer (e.g., estrogen receptor positive or negative, progesterone receptor positive or negative, HER-2 positive or negative, triple-negative breast cancer, or BRCA1 and/or BRCA2 positive or negative), lung cancer (e.g., non-small cell lung cancer and small cell lung cancer), ovarian cancer, endometrial cancer, prostate cancer, pharyngeal cancer, esophageal cancer, glioblastoma, adrenal cancer, B-cell malignancies, biliary tract cancer, bladder cancer, bone cancer, brain cancer, cervical cancer, choriocarcinoma, colon cancer, colorectal cancer, connective tissue cancer, cancer of the digestive system, gallbladder cancer, gastric cancer, cancer of the head and neck, hepatocellular carcinoma, intra-epithelial neoplasm, kidney cancer, liver cancer, lymphoma, skin cancer (e.g., melanoma and basal cell carcinoma), neuroblastoma, mesothelioma, neuroglioma, oral cavity cancer, pediatric cancer, pancreatic cancer, pancreatic endocrine tumors, pituitary adenoma, thymoma, renal cell carcinoma, cancer of the respiratory system, salivary gland cancer, sarcoma (e.g., Ewing's sarcoma, fibrosarcoma, and rhabdomyosarcoma), small bowel cancer, testicular cancer, thyroid cancer, ureteral cancer, cancer of the urinary system, and hematological cancers (e.g., acute myeloid leukemia and multiple myeloma).

Kits

The invention also provides kits that include a container with eribulin (e.g., eribulin mesylate), a container with a PARP inhibitor (e.g., E7449 (or a pharmaceutically acceptable salt thereof (e.g., the L-tartrate salt)), and/or a container with a platinum-based antineoplastic agent (e.g., carboplatin). The drugs in the kits may be provided in amounts sufficient to treat cancer in a patient in need thereof (e.g., amounts sufficient for a single administration or for multiple administrations; see above). The kits may thus include multiple containers that each include effective amounts of single-dose eribulin (e.g., eribulin mesylate), PARP inhibitor (e.g., E7449 (or a pharmaceutically acceptable salt thereof (e.g., the L-tartrate salt)), and/or platinum-based antineoplastic drug (e.g., carboplatin) pharmaceutical composition(s). Optionally, instruments and/or devices necessary for administering the pharmaceutical composition(s) may also be included in the kits. Furthermore, the kits may include additional components, such as instructions or administration schedules, for treating a patient with cancer with the drugs.

The present invention is illustrated by the following examples, which are in no way intended to be limiting of the invention.

EXPERIMENTAL EXAMPLES

Example 1

Effect of E7449 in Combination with Eribulin Mesylate and/or Carboplatin on Growth of Subcutaneous Human Breast Cancer MDA-MB-436 Xenografts in SCID Mice Summary The effect of E7449 in combination with E7389 (eribulin mesylate) and/or carboplatin was examined in subcutaneous human breast cancer MDA-MB-436 xenografts in SCID mice. Three separate studies were performed. In the first study, treatment groups included E7449 (60 mg/kg) and E7389 (0.4 or 1.6 mg/kg) as single agents and 2 groups treated with the combination. E7449 was orally administered once daily at 60 mg/kg for 28 days and E7389 was intravenously administered at 0.4 or 1.6 mg/kg once every 4 days, 4 times. In the second study, treatment groups included E7449 (60 mg/kg) and carboplatin (15 or 60 mg/kg) as single agents and 2 groups treated with the combination. E7449 was orally administered once daily at 60 mg/kg for 28 days and carboplatin was intravenously administered at 15 or 60 mg/kg once, on the first day of drug treatment. In the third study, treatment groups included E7449 (60 mg/kg), E7389 (0.2 mg/kg) and carboplatin (7.5 mg/kg) as single agents, 3 groups treated with two-drug combinations (E7449+E7389, E7449+carboplatin and E7389+carboplatin) and a group treated with the three-drug combination. Antitumor activity was observed for E7449 (60 mg/kg) as a single agent in this model. Dose-dependent antitumor activity was observed following treatment with E7389 alone: a modest antitumor effect was observed at 0.4 mg/kg while tumor regression was observed following treatment at the 1.6 mg/kg dose. Combination of E7449 and E7389 (0.4 mg/kg) resulted in a statistically significant increased antitumor effect versus either E7449 or E7389 alone. Since tumor regression was observed in mice treated with E7389 at 1.6 mg/kg, effects of E7449 combination were not assessed at this dose. Dose-dependent antitumor activity was observed following treatment with carboplatin alone at 15 and 60 mg/kg. Combination of E7449 and carboplatin at 15 or 60 mg/kg resulted in a statistically significant increased antitumor effect versus either E7449 or carboplatin alone. Treatment of MDA-MB-436 xenografts with the triple combination of E7449+E7389+ carboplatin resulted in greater antitumor activity than single agent and 2-drug combination treatments (statistical significance not reached versus E7449+E7389 or versus E7449+ carboplatin combinations). All drug treatments as single agents and in combination were well tolerated without any deaths or significant body weight loss.

Objective

The purpose of this study was to investigate the combination activity of E7449 treatment with E7389 and/or carboplatin on the growth of subcutaneously implanted MDA-MB-436 human breast cancer cells in SCID mice.

Materials and Methods

The vehicle for E7449 was 0.5% methyl cellulose. E7449 powder was ground using a mortar and pestle. Vehicle was gradually added and mixed with the compound to make a 6 mg/mL stock solution. Solutions were divided into aliquots and stored at 4° C. for up to 7 days.

The vehicle for eribulin mesylate (E7389) was saline (0.9% sodium chloride). E7389 stock solution (0.5 mg/mL) was diluted with vehicle to concentrations of 0.02, 0.04, and 0.16 mg/mL. E7389 was formulated fresh on each day of treatment.

The vehicle for carboplatin was saline (0.9% sodium chloride). Carboplatin powder (50 mg) was dissolved in 8.33 mL saline to make a stock solution of 6 mg/mL. Stock solution was diluted with vehicle to concentrations of 1.5 mg/mL. For 0.75 mg/mL stock solution 6 mg carboplatin was dissolved in 8 mL saline. Carboplatin was formulated fresh on the day of treatment.

The cells used were human breast cancer cells MDA-MB-436 (ATCC® HTB-130™; American Type Culture Collection (ATCC); Manassas, Va.).

The mice used were female, 5-6 week old, C.B.17 SCID mice Charles River (Wilmington, Mass.) (for E7449 +eribulin and E7449 +carboplatin study), Taconic (Hudson, N.Y.) (for triple combination study).

measured and mice were randomized into the 6 treatment groups based on tumor volume (average of 300 mm$^3$). Following randomization, drug treatment was initiated. Groups A to D were composed of 5 mice and groups E and F consisted of 4 mice for a total of 28 mice on the first day of treatment. E7449 was formulated in 0.5% methyl cellulose and orally administered once daily for 28 days (starting on Day 58) at 60 mg/kg based on body weight at 0.1 mL per 10 g. E7389 was formulated in saline and was intravenously administered once every 4 days, 4 times (Day 58, 62, 66, and 70) at a dosage of 0.4 or 1.6 mg/kg as single agent or in combination with E7449, based on body weight at 0.1 mL per 10 g. The control group was treated with oral vehicle (0.5% methyl cellulose in water) daily and intravenous vehicle (saline) once every 4 days, 4 times. E7449 or vehicle was administered first and when dosing of all animals was complete, E7389 was administered to animals receiving the combination.

TABLE 1

Treatment Groups for Investigation of Effect of E7449 and E7389 Alone and in Combination in MDA-MB-436 Human Breast Cancer Xenografts in SCID Mice

| Group Number | Treatment | Route | Schedule | No. of Animals |
|---|---|---|---|---|
| A | Vehicle (0.5% methyl cellulose) + Vehicle (saline) | PO + IV | QDx28, Q4Dx4 | 5 |
| B | E7389 1.6 mg/kg | IV | Q4Dx4 | 5 |
| C | E7449 60 mg/kg | PO | QDx28 | 5 |
| D | E7449 60 mg/kg + E7389 1.6 mg/kg | PO + IV | QDx28, Q4Dx4 | 5 |
| E | E7389 0.4 mg/kg | IV | Q4Dx4 | 4 |
| F | E7449 60 mg/kg + E7389 0.4 mg/kg | PO + IV | QDx28, Q4Dx4 | 4 |

Measurement of Antitumor Activity

MDA-MB-436 human triple negative breast cancer cells are BRCA1 mutant and PTEN null. Cells were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and resuspended in ice-cold PBS. Female immunodeficient SCID mice were inoculated subcutaneously near the right axillary area with MDA-MB-436 cells ($5\times10^6$) in a 1:1 ratio (50 µL each) with Matrigel™ in a volume of 0.1 mL in phosphate buffered saline, using a 26-gauge needle. A total of 125 mice, approximately 6 weeks old were implanted with MDA-MB-436 cells.

E7449, carboplatin and E7389 were evaluated as single agents and in combination for antitumor activity against MDA-MB-436 human breast cancer xenografts in SCID mice. Three separate studies were performed. The first experiment consisted of a vehicle control group, an E7449 single agent group, two groups treated with single agent E7389 and 2 combination drug-treated groups (Table 1). Thirty mice were inoculated with MDA-MB-436 cells and on Day 58 following implantation, tumor volumes were The second experiment consisted of a vehicle control group, an E7449 single agent group, 2 groups treated with single agent carboplatin, and 2 combination drug-treated groups (Table 2). Thirty-five mice were inoculated with MDA-MB-436 cells and on Day 57, following implantation, tumor volumes were measured and mice were randomized into 6 treatment groups based on tumor volume (average of 250 mm$^3$). Following randomization drug treatment was initiated. Groups A to D were composed of 5 mice and groups E and F consisted of 6 mice for a total of 32 mice on the first day of treatment. E7449, formulated in 0.5% methyl cellulose was orally administered daily for 28 days (starting on Day 57), at 60 mg/kg based on body weight at 0.1 mL per 10 g. Carboplatin was formulated in saline and was intravenously administered once on the first day of treatment (Day 57) at a dosage of 15 or 60 mg/kg as a single agent or in combination with E7449 based on body weight at 0.1 mL per 10 g. The control group was treated with oral vehicle (0.5% methyl cellulose in water) daily and intravenous vehicle (saline) once on Day 57. E7449 or vehicle was administered first, and when dosing of all animals was complete carboplatin was administered to animals receiving the combination.

TABLE 2

Treatment Groups for Investigation of Effect of E7449 and Carboplatin Alone and in Combination in MDA-MB-436 Human Breast Cancer Xenografts in SCID Mice

| Group Number | Treatment | Route | Schedule | No. of Animals |
|---|---|---|---|---|
| A | Vehicle (0.5% methyl cellulose) + Vehicle (saline) | PO + IV | QDx28, QDx1 | 5 |

TABLE 2-continued

Treatment Groups for Investigation of Effect of E7449 and Carboplatin Alone and in Combination in MDA-MB-436 Human Breast Cancer Xenografts in SCID Mice

| Group Number | Treatment | Route | Schedule | No. of Animals |
|---|---|---|---|---|
| B | E7449 60 mg/kg | PO | QDx28 | 5 |
| C | Carboplatin 60 mg/kg | IV | QDx1 | 5 |
| D | Carboplatin 15 mg/kg | IV | QDx1 | 5 |
| E | E7449 60 mg/kg + Carboplatin 60 mg/kg | PO + IV | QDx28, QDx1 | 6 |
| F | E7449 60 mg/kg + Carboplatin 15 mg/kg | PO + IV | QDx28, QDx1 | 6 |

The third experiment consisted of a vehicle control group, 3 groups treated with single agent E7449, E7389, or carboplatin, 3 groups treated with double combinations of E7449+E7389, E7449+carboplatin, and E7389+carboplatin and a group treated with the three-drug combination (Table 3). Sixty mice were inoculated with MDA-MB-436 cells and on Day 41 following implantation, tumor volumes were measured and mice were randomized into 8 treatment groups based on tumor volume (average of 250 mm$^3$). Following randomization drug treatment was initiated. Each group consisted of 6 mice for a total of 48 mice on the first day of treatment (Day 41). E7449, formulated in 0.5% methyl cellulose, was orally administered daily for 28 days (starting on Day 41), at 60 mg/kg based on body weight at 0.1 mL per 10 g. E7389 was formulated in saline and intravenously administered once every 4 days, 4 times (Days 41, 45, 49, and 53) at a dosage of 0.2 mg/kg. Carboplatin was formulated in saline and intravenously administered once on the first day of treatment (Day 41) at a dosage of 7.5 mg/kg based on body weight at 0.1 mL per 10 g. The control group was treated with oral vehicle (0.5% methyl cellulose in water) daily and intravenous vehicle (saline) once every 4 days, 4 times. E7449 or vehicle was administered first and when dosing of all animals was complete, E7389 and finally carboplatin was administered to animals receiving the combination.

TABLE 3

Treatment Groups for Investigation of Effect of E7449, E7389 and Carboplatin Alone and in Combinations in MDA-MB-436 Human Breast Cancer Xenografts in SCID Mice

| Group Number | Treatment | Route | Schedule | No. of Animals |
|---|---|---|---|---|
| A | Vehicle (0.5% methyl cellulose) + Vehicle (saline) | PO + IV | QDx28, Q4Dx4 | 6 |
| B | E7449 60 mg/kg | PO | QDx28 | 6 |
| C | E7389 0.2 mg/kg | IV | Q4Dx4 | 6 |
| D | Carboplatin 7.5 mg/kg | IV | QDx1 | 6 |
| E | E7449 60 mg/kg + E7389 0.2 mg/kg | PO + IV | QDx28, Q4Dx4 | 6 |
| F | E7449 60 mg/kg + Carboplatin 7.5 mg/kg + E7389 0.2 mg/kg | PO + IV | QDx28, QDx1, Q4Dx4 | 6 |
| G | E7449 60 mg/kg + Carboplatin 7.5 mg/kg | PO + IV | QDx28, QDx1 | 6 |
| H | E7389 0.2 mg/kg + Carboplatin 7.5 mg/kg | IV + IV | Q4Dx4, QDx1 | 6 |

The general health of the mice was monitored and mortality recorded daily. Tumor volume was determined by caliper (Mitutoyo, Aurora, Ill.) measurements (mm) using the formula (l×w$^2$)/2=mm$^3$, where l and w refer to the larger and smaller perpendicular dimensions collected at each measurement. Tumor dimensions and body weights were recorded twice per week starting on the first day of treatment.

Relative body weight was calculated as follows: Relative body weight=(body weight on day of measurement/body weight on first day of treatment). The data generated consist of group mean tumor volumes at each measurement and group mean body weights at each measurement. The mean±SEM for tumor volume and mean±SEM for relative body weight for each experimental group was calculated.

Drug treatment was initiated 58, 57, or 41 days post tumor implantation, in the E7449+E7389, E7449+carboplatin, and triple combination studies respectively, and continued for 28 days. Animals whose tumor measurement reached ≥2 cm at the longest axis or whose tumor became ulcerated were euthanized prior to study termination. The studies were terminated on Days 108, 105, and 84 (E7389, carboplatin and triple combination respectively).

Statistical Analysis

Statistical analysis of vehicle groups versus all drug-treated groups was performed by a one way analysis of variance (ANOVA) for tumor volume followed by Dunnett's multiple comparisons test for all 3 studies. Statistical analyses were performed for all studies (Day 81 for the E7449+E7389 combination, Day 93 for the E7449 +carboplatin combination study, and Day 61 for the triple combination study). A value of P<0.05 was considered statistically significant under a two-sided hypothesis. Unpaired t-test analyses were also to compare tumor volumes following treatment with combinations of E7449+E7389 versus single agents in the first study on Day 81, and E7449+carboplatin versus single agents on Day 93 in the second study. In the triple combination study, an unpaired t-test analysis was also performed to compare tumor volumes on Day 61 following treatment with the 3 two-drug combinations (E744930 E7389, E7449+carboplatin, and E7389+carboplatin) (groups E, G, and H) versus the triple combination (group F). All statistical analyses were performed using Graph Pad Prism 6 software (Lake Forest, Calif.).

Results

Figure 2:
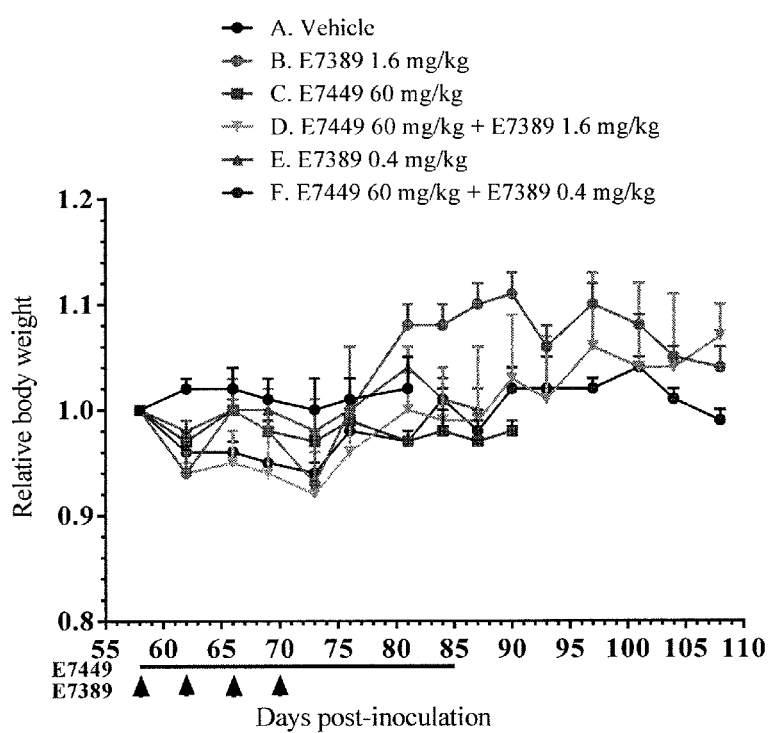
FIG. 2 is a graph showing relative body weights of mice treated with E7449 and E7389 alone and in combination in MDA-MB-436 human breast cancer xenografts in SCID mice. Relative body weight for the indicated treatment groups is shown as a function of time post inoculation.

FIG. 1 shows the effect of E7449 and E7389 as single agents and in combination in MDA-MB-436 human breast cancer xenografts in SCID mice. Administration of single agent E7449 at 60 mg/kg resulted in modest and statistically significant tumor growth inhibition. Dose dependent antitumor activity was observed with E7389 as single agent. A modest antitumor effect was observed with treatment at 0.4 mg/kg, while E7389 dosed at 1.6 mg/kg resulted in tumor regression. Combination of E7449 and E7389 at 0.4 mg/kg resulted in tumor regression and significantly delayed tumor progression versus treatment with E7449 or E7389 alone (FIG. 1). Since tumor regression was observed in mice treated with single agent E7389 at 1.6 mg/kg, effects of E7449 combination were not assessed at this dose. Administration of drugs as single agents or in combination had no significant effect on body weight (FIG. 2).

Data represent the mean±SEM. Final tumor volume measurements were reported for vehicle, E7449 single agent and E7389 (0.4 mg/kg) single agent-treated mice (groups A, C, and E) on Days 81, 90, and 87 respectively: mice were euthanized because of large or ulcerated tumors. Drug treatment stopped on Day 85 and the study was terminated on Day 108. Significant antitumor activity was observed for all drug treatment groups: *P<0.05 versus vehicle on Day 81 (one-way ANOVA followed by Dunnett's multiple comparisons test)). Tumor growth was significantly decreased with the combination of E7449+E7389 (0.4 mg/kg) versus E7449 or E7389 treatment alone (Groups F versus C and E), #P<0.05 unpaired t-test on Day 81.

Final body weight measurements were reported for vehicle, E7449 single agent, and E7389 (0.4 mg/kg) single agent-treated mice (groups A, C, and E) on Days 81, 90, and 87, respectively. Mice were then euthanized because of large or ulcerated tumors. Drug treatment stopped on Day 85 and the study was terminated on Day 108. No significant body weight loss was observed in any of the drug treatment groups over the course of the study.

Figure 3:
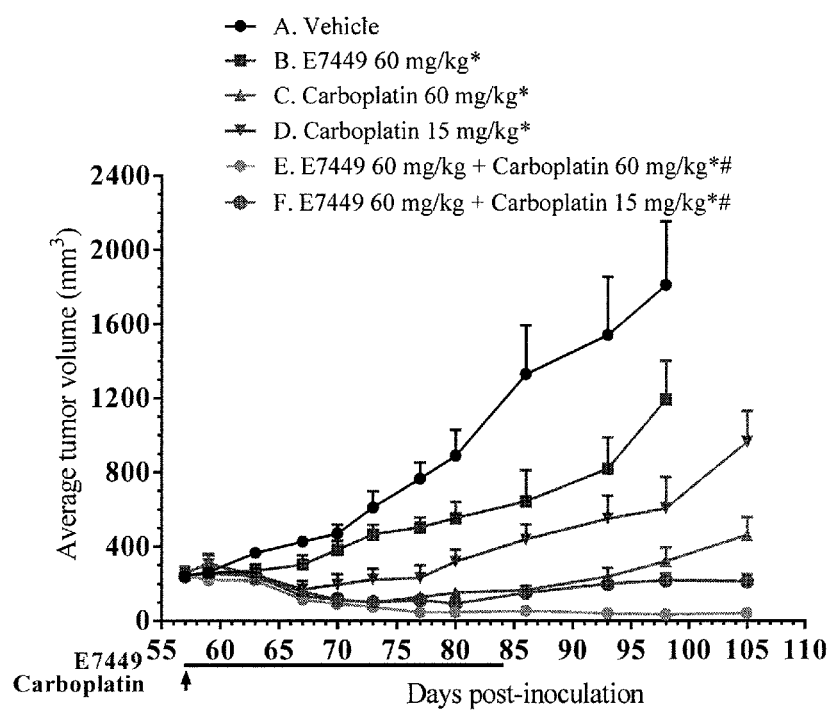
FIG. 3 is a graph showing an antitumor effect of E7449 and carboplatin alone and in combination in MDA-MB-436 human breast cancer xenografts in SCID mice. Average tumor volume for the indicated treatment groups is shown as a function of time post inoculation.
Figure 4:
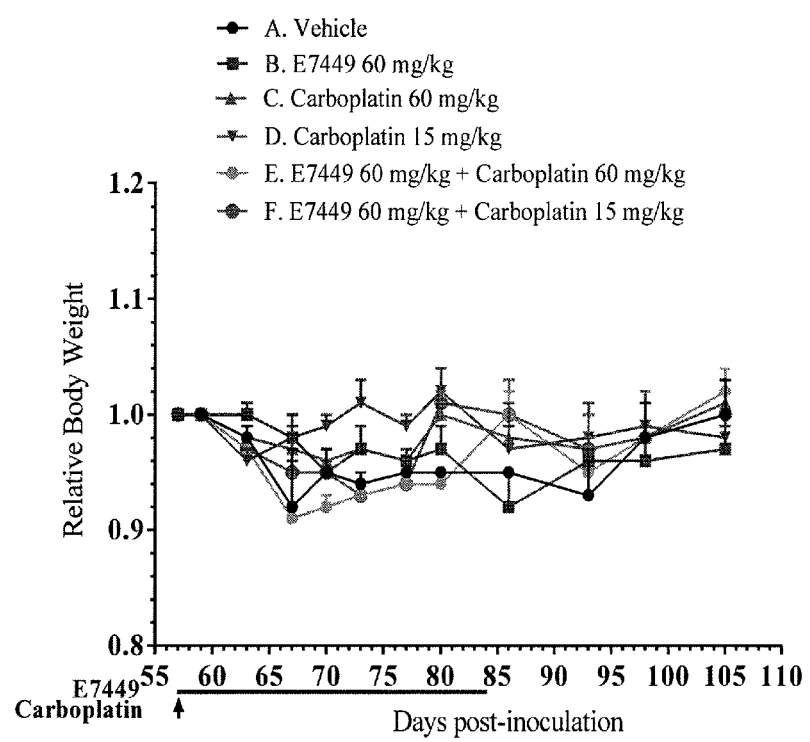
FIG. 4 is a graph showing relative body weights of mice treated with E7449 and carboplatin alone and in combination in MDA-MB-436 human breast cancer xenografts in SCID mice. Relative body weight for the indicated treatment groups is shown as a function of time post inoculation.

FIG. 3 shows the effect of E7449 and carboplatin as single agents and in combination in MDA-MB-436 human breast cancer xenografts in SCID mice. Administration of single agent E7449 at 60 mg/kg resulted in modest and statistically significant tumor growth inhibition. Dose-dependent antitumor activity was observed with carboplatin as single agent (15 and 60 mg/kg). Combination of E7449 (60 mg/kg) and carboplatin at either dose enhanced the antitumor activity versus carboplatin or E7449 alone (FIG. 3). Administration of either drug as single agent or both drugs in combination had no significant effect on body weight (FIG. 4).

Data represent the mean±SEM. Final tumor volume measurements were reported for vehicle and for single agent E7449-treated (groups A and B) on Day 98. Mice were euthanized because of large or ulcerated tumors. Drug treatment stopped on Day 84 and the study was terminated on Day 105. Statistically significant inhibition of tumor growth was observed for all drug treatment groups: *P<0.05 versus vehicle on Day 93 (one-way ANOVA followed by Dunnett's multiple comparisons test). Combination treatment with E7449+carboplatin at 15 or 60 mg/kg (groups F and E) resulted in significantly increased antitumor activity versus single agent treatments of E7449 or carboplatin (15 or 60 mg/kg) (groups B, D, and C), #P<0.05 unpaired t-test on Day 93.

Data represent the mean±SEM. Data represent the mean±SEM. Final body weight measurements were reported for vehicle and for single agent E7449-treated (groups A and B) on Day 98: mice were euthanized because of large or ulcerated tumors. Drug treatment stopped on Day 84 and the study was terminated on Day 105. No significant body weight loss was observed in any of the drug treatment groups over the course of the study.

Figure 5:
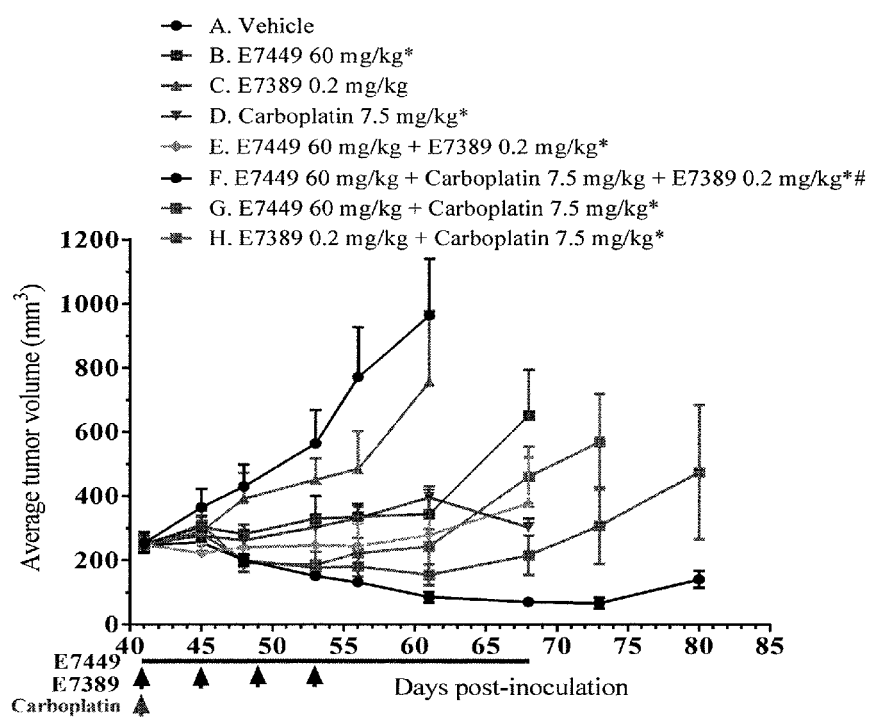
FIG. 5 is a graph showing an antitumor effect of E7449, E7389, and carboplatin alone and in combinations in MDA-MB-436 human breast cancer xenografts in SCID mice. Average tumor volume for the indicated treatment groups is shown as a function of time post inoculation.
Figure 6:
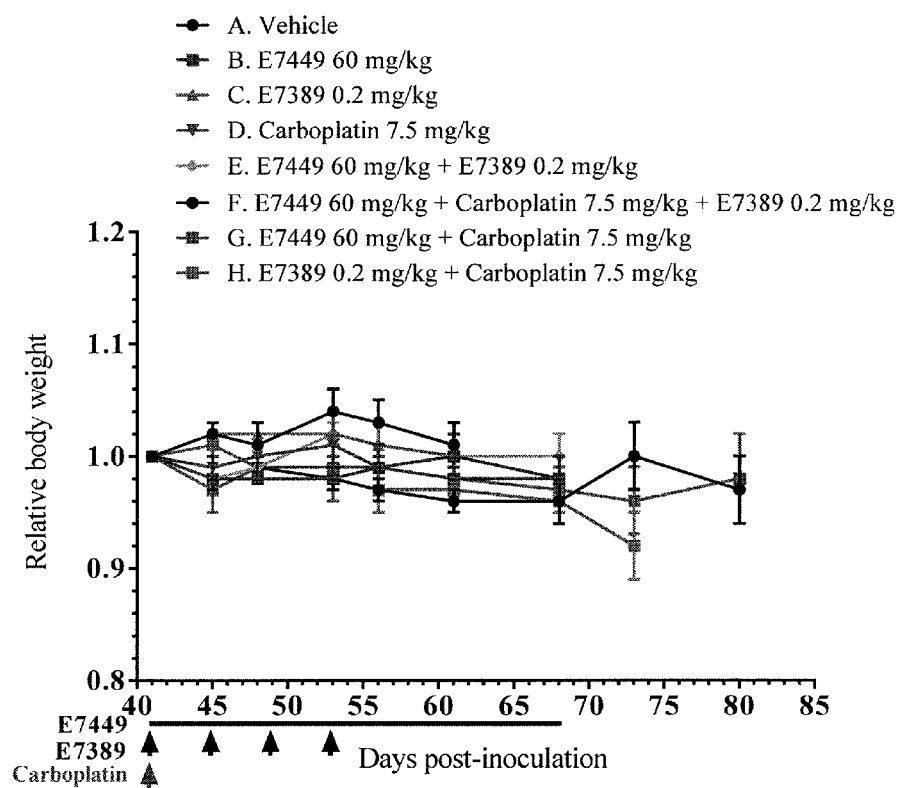
FIG. 6 is a graph showing relative body weights of mice treated with E7449, E7389, and carboplatin alone and in combinations in MDA-MB-436 human breast cancer xenografts in SCID mice. Relative body weight for the indicated treatment groups is shown as a function of time post inoculation.

FIG. 5 shows the effect of E7449, E7389 and carboplatin as single agents, in 2-drug combinations (E7449+E7389, E7449+carboplatin, and E7389+carboplatin) and in the 3-drug combination in MDA-MB-436 human breast cancer xenografts in SCID mice. Administration of single agent E7449 at 60 mg/kg or carboplatin at 7.5 mg/kg resulted in statistically significant tumor growth inhibition. Treatment with single agent E7389 at 0.2 mg/kg did not significantly inhibit tumor growth. Significant antitumor activity was observed with E7449 and carboplatin as single agents and all 2-drug combinations. The 3-drug combination was most effective and resulted in tumor regression and delayed re-growth of tumors (statistically significant only against the E7389+carboplatin 2-drug combination) (FIG. 5). Administration of drugs as single agents or in combination had no significant effect on body weight (FIG. 6).

Data represent the mean±SEM. Final tumor volume measurements were reported for vehicle and single agent E7389-treated mice (groups A and C) on Day 61 and for single agent E7449- and E7449+E7389-treated mice (groups B and E) on Day 68: mice were euthanized because of large or ulcerated tumors. Drug treatment stopped on Day 68 and the study was terminated on Day 84. Administration of E7389 at 0.2 mg/kg did not inhibit tumor growth. Statistically significant inhibition of tumor growth was observed for all other drug treatment groups: *P<0.05 versus vehicle on Day 61 (one-way ANOVA followed by Dunnett's multiple comparisons test). Administration of the 3-drug combination resulted in increased tumor growth inhibition versus all other treatment groups (statistically significant only against the E7389+carboplatin 2-drug combination; #P<0.05 on Day 61 (unpaired t-test).

Data represent the mean±SEM. Final body weight measurements were reported for vehicle and single agent E7389-treated mice (groups A and C) on Day 61 and for single agent E7449- and E7449+E7389-treated mice (groups B and E) on Day 68. Mice were euthanized because of large or ulcerated tumors. Drug treatment stopped on Day 68 and the study was terminated on Day 84. No significant body weight loss was observed in any of the drug treatment groups over the course of the study.

Conclusion

E7449 demonstrated significant antitumor activity as a single agent following 28 day dosing at 60 mg/kg in the BRCA1 mutant and PTEN null MDA-MB-436 human triple negative breast cancer xenograft model in SCID mice. Dose-dependent antitumor activity was observed following treatment with E7389 alone: a modest antitumor effect was observed at 0.4 mg/kg while tumor regression was observed following treatment at the 1.6 mg/kg dose. Combination of E7449 and E7389 (0.4 mg/kg) resulted in a statistically significant increased antitumor effect versus either E7449 or E7389 alone. Since tumor regression was observed in mice treated with E7389 at 1.6 mg/kg, effects of E7449 combination were not assessed at this dose. Treatment with single agent carboplatin at dosage levels of 15 and 60 mg/kg (QDx1) resulted in dose-dependent anticancer activity. Combination with E7449 enhanced the antitumor effect of carboplatin at 15 or 60 mg/kg versus either E7449 or carboplatin alone in this model. Treatment of MDA-MB-436 xenografts with the triple combination of E7449+E7389+carboplatin resulted in greater antitumor activity than single agent and 2-drug combination treatments (statistical significance not reached versus E7449+E7389 or versus E7449+carboplatin combinations). No significant toxicity as indicated by body weight loss was observed for any of the drug treatments as single agents or in combination.

Example 2

Effect of E7449 in Combination with Eribulin Mesylate on Growth of Subcutaneous Human Breast Cancer MDA-MB-468 Xenografts in Athymic Mice Summary The effect of E7449 in combination with E7389 (eribulin mesylate) was examined in a subcutaneous human breast cancer MDA-MB-468 xenograft model in athymic mice. Treatment groups included E7449 (100 mg/kg) and E7389 (0.1 or 0.4 mg/kg) as single agents and 2 groups treated with the drug combinations. E7449 was orally administered once daily at 100 mg/kg for 28 days and E7389 was intravenously administered at 0.1 or 0.4 mg/kg once every 4 days, 3 times. E7449 as a single agent lacked significant antitumor activity in this model. Dose-dependent tumor regression was observed following treatment with E7389 alone at the 0.1 and 0.4 mg/kg doses. All mice treated with E7389 at 0.4 mg/kg were tumor-free at study termination. Addition of E7449 to E7389 at 0.1 mg/kg resulted in a statistically significant delayed time to tumor progression. Since mice treated with E7389 at 0.4 mg/kg were tumor-free at study termination, effects of E7449 combination could not be assessed at this dose. Combination treatments were well tolerated: maximal mean body weight loss (7%) observed with E7389 treatment at 0.4 mg/kg was not exacerbated by addition of E7449. All mice regained body weight on completion of drug treatment.

Objective

The purpose of this study was to investigate the combination activity of treatment with E7449 and E7389 on the growth of subcutaneously implanted MDA-MB-468 human breast cancer cells in athymic mice.

Materials and Methods

The vehicle for E7449 was 0.5% methyl cellulose. E7449 powder was ground using a mortar and pestle. Vehicle was gradually added and mixed with the compound to make a stock 10 mg/mL solution. The stock solution was divided into aliquots and stored at 4° C. for up to 7 days.

The vehicle for E7389 was saline (0.9% sodium chloride). E7389 stock solution (0.5 mg/mL) was diluted with vehicle to concentrations of 0.04 and 0.01 mg/mL. E7389 was formulated fresh on each day of treatment.

The cells used were human breast cancer cells, MDA-MB-468 (ATCC® HTB-132™), American Type Culture Collection (ATCC).

The mice used were female, 6 week old, CrTac:NCr-Foxnr", Taconic, Hudson, N.Y.

Measurement of Antitumor Activity

MDA-MB-468 human triple negative breast cancer cells are wild type for BRCA1 and 2 and PTEN null. Cells were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and resuspended in ice-cold PBS. Female immunodeficient athymic mice were inoculated subcutaneously near the right axillary area with MDA-MB-468 cells ($5 \times 10^6$) in a 1:1 ratio (50 μL each) with matrigel in a volume of 0.1 mL in phosphate buffered saline using a 26-gauge needle. A total of 60 mice, approximately 8 weeks old were implanted with MDA-MB-468 cells.

E7449 and E7389 were evaluated as single agents and in combination for antitumor activity against MDA-MB-468 human breast cancer xenografts in athymic mice. The experiment consisted of a vehicle control group, an E7449 single agent group, two groups treated with single agent E7389 and 2 combination drug-treated groups (Table 4). Sixty mice were inoculated with MDA-MB-468 cells. On day 7 following implantation, tumor volumes were measured and mice were randomized into the 6 treatment groups based on tumor volume (average of 180 $mm^3$). Following randomization drug treatment was initiated. Each group was composed of 6 mice for a total of 36 mice on the first day of treatment. E7449 was formulated in 0.5% methyl cellulose and orally administered daily at 100 mg/kg based on body weight at 0.1 mL per 10 g. E7449 was administered once daily for 28 days (starting on Day 7) as a single agent or in combination. E7389 was formulated in saline and was intravenously administered once every 4 days, 3 times (Day 7, 11, and 15) at a dosage of 0.1 or 0.4 mg/kg as single agent or in combination with E7449, based on body weight at 0.1 mL per 10 g. The control group was treated with oral vehicle (0.5% methyl cellulose in water) daily and intravenous vehicle (saline) once every 4 days, 3 times. E7449 or vehicle was administered first and when dosing of all animals was complete, E7389 was administered to animals receiving the combination.

The general health of the mice was monitored and mortality recorded daily. Tumor volume was determined by caliper (Mitutoyo, Aurora, Ill.) measurements (mm) using the formula $(l \times w^2)/2 = mm^3$, where l and w refer to the larger and smaller perpendicular dimensions collected at each measurement. Tumor dimensions and body weights were recorded twice per week starting on the first day of treatment. Relative body weight was calculated as follows: Relative body weight=body weight on day of measurement/body weight on first day of treatment). The data generated consist of group mean tumor volumes at each measurement and group mean body weights at each measurement. The mean±SEM for tumor volume and mean±SEM for relative body weight for each experimental group was calculated.

Drug treatment was initiated 7 days post tumor implantation and continued for 28 days. Animals whose tumor measurement reached cm at the longest axis or whose tumor became ulcerated were euthanized prior to study termination. The study was terminated on Day 52. Statistical analysis was performed on Days 35 and 52.

TABLE 4

Treatment Groups for Investigation of Effect of E7449 and E7389 Alone and in Combination in MDA-MB-468 Human Breast Cancer Xenografts in Athymic Mice

| Group Number | Treatment | Route | Schedule | No. of Animals |
|---|---|---|---|---|
| A | Vehicle (0.5% methyl cellulose) + Vehicle (saline) | PO + IV | QDx28, Q4Dx3 | 6 |
| B | E7449 100 mg/kg | PO | QDx28 | 6 |
| C | E7389 0.4 mg/kg | IV | Q4Dx3 | 6 |
| D | E7389 0.1 mg/kg | IV | Q4Dx3 | 6 |
| E | E7449 100 mg/kg + E7389 0.4 mg/kg | PO + IV | QDx28, Q4Dx3 | 6 |
| F | E7449 100 mg/kg + E7389 0.1 mg/kg | PO + IV | QDx28, Q4Dx3 | 6 |

Statistical Analysis

Statistical analysis of the vehicle group (A) versus the drug-treated groups (B, C, D, E, and F) was performed by a one way analysis of variance (ANOVA) for tumor volume followed by Dunnett's multiple comparisons test. The analysis was performed at vehicle endpoint on Day 35 of the study. A value of $P<0.05$ was considered statistically significant under a two-sided hypothesis. An unpaired t-test analysis was also performed for tumor volume to compare tumor re-growth on Day 52 following treatment with E7389 (0.1 mg/kg) alone or in combination with E7449 (groups D and F). All statistical analyses were performed using GraphPad Prism 6 software (Lake Forest, Calif.).

Results

Figure 7:
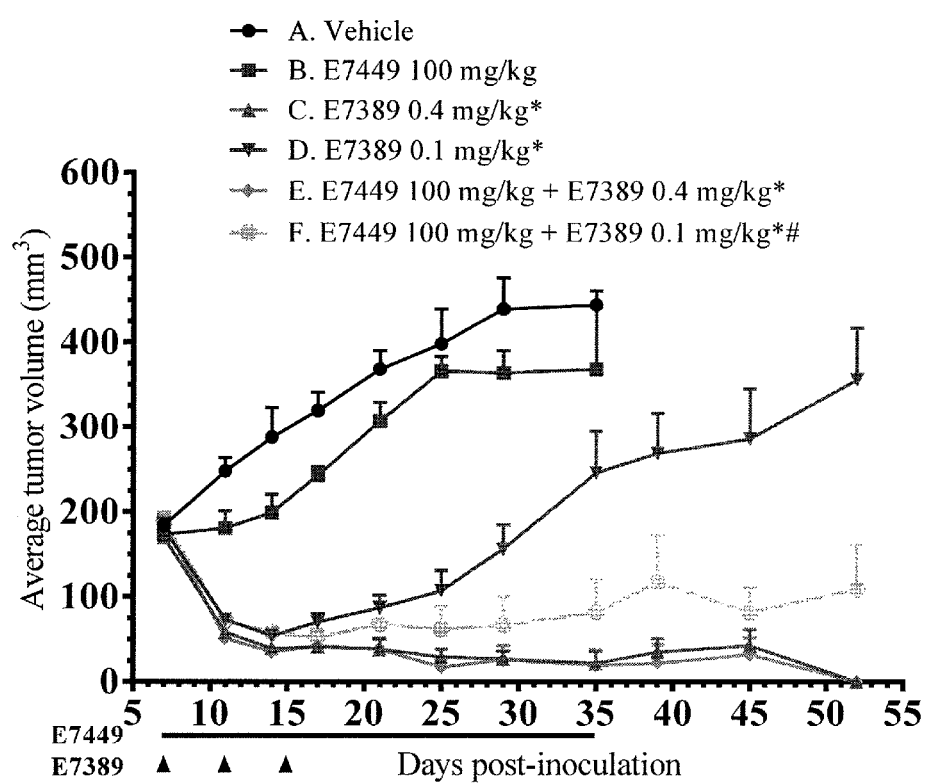
FIG. 7 is a graph showing an antitumor effect of E7449 and E7389 alone and in combination in MDA-MB-468 human breast cancer xenografts in athymic mice. Average tumor volume for the indicated treatment groups is shown as a function of time post inoculation.
Figure 8:
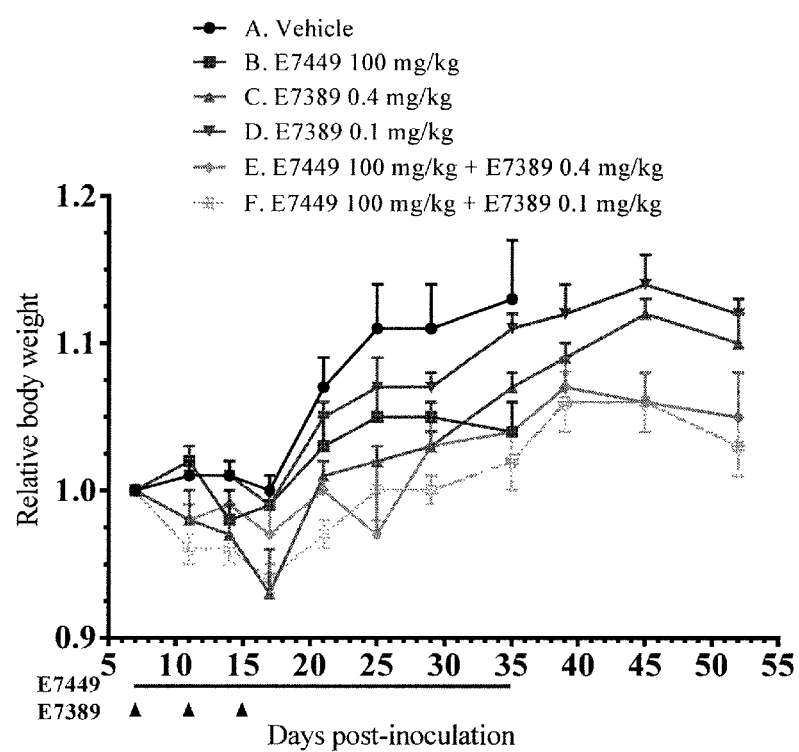
FIG. 8 is a graph showing relative body weights of mice treated with E7449 and E7389 alone and in combination in MDA-MB-468 human breast cancer xenografts in athymic mice. Relative body weight for the indicated treatment groups is shown as a function of time post inoculation.

FIG. 7 shows the effect of E7449 and E7389 as single agents and in combination in MDA-MB-468 human breast cancer xenografts in athymic mice. Administration of single agent E7449 at 100 mg/kg did not significantly inhibit tumor growth. Tumor regression was observed with E7389 as single agent at both dosages (0.1 and 0.4 mg/kg). Tumor re-growth following treatment was dose-dependent; tumors in mice treated with 0.1 mg/kg began re-growing within days of final E7389 dose whereas mice treated with 0.4 mg/kg became tumor-free with no palpable tumors observed up to the date of study termination (Day 52). Combination treatment with E7449 and E7389 at 0.1 mg/kg significantly delayed the time to tumor progression versus treatment with E7389 alone (FIG. 7). The effect of combining E7449 and E7389 at 0.4 mg/kg could not be determined because treatment with single agent E7389 at this dosage resulted in tumor-free mice. Administration of E7389 at 0.4 mg/kg resulted in a maximal mean body weight loss of 7% on Day 17 (FIG. 8). Toxicity was not exacerbated by combination with E7449 and all mice regained body weight on completion of drug treatment.

Data represent the mean±SEM. Final tumor volume measurements were reported for vehicle treated and single agent E7449 treated mice (groups A and B) on Day 35: mice were then euthanized because of ulcerated tumors. Drug treatment stopped on Day 35 and the study was terminated on Day 52. No antitumor activity was observed for E7449 alone. Statistically significant inhibition of tumor growth was observed for all other treatment groups: *P<0.0001 versus vehicle on Day 35 (one-way ANOVA followed by Dunnett's multiple comparisons test). Tumor progression was significantly decreased in the E7389 (0.1 mg/kg)+E7449 combination treated group versus E7389 alone (group F versus D): #P=0.012 on Day 52 (unpaired t-test).

Data show the mean±SEM. Final body weight measurements were reported for vehicle treated and single agent E7449 treated mice (groups A and B) on Day 35: mice were then euthanized because of ulcerated tumors. Drug treatment stopped on Day 35 and the study was terminated on Day 52.

Maximum mean body weight loss of 7% was observed on Day 17 in the E7389 0.4 mg/kg treated group (C). Body weight loss was not exacerbated by addition of E7449 to E7389 (groups E and F). Recovery from body weight loss was observed in all mice upon completion of drug treatment.

Conclusion

E7449 did not demonstrate significant antitumor activity as a single agent following 28 day dosing at 100 mg/kg in the BRCA wild type and PTEN null MDA-MB-468 human triple negative breast cancer xenograft model in athymic mice. Single agent E7389 at dosage levels of 0.1 and 0.4 mg/kg (Q4D×3) resulted in statistically significant and dose-dependent anticancer activity with tumor-free mice obtained at the higher dose. Combination of E7389 with E7449 resulted in a delayed tumor progression versus treatment with E7389 (0.1 mg/kg) alone. Combination effect was not evaluable at the higher dose since mice were tumor-free following E7389 treatment alone. No exacerbation of toxicity as indicated by body weight loss was observed for the combination drug treatment.

Example 3

Effect of E7449 in Combination with Eribulin Mesylate or Carboplatin on Growth of Subcutaneous Human Breast Cancer MDA-MB-231 Xenografts in Athymic Mice Summary The effect of E7449 in combination with E7389 (eribulin mesylate) or carboplatin was examined in subcutaneous human breast cancer MDA-MB-231 xenografts in athymic mice. Two separate studies were performed. In the first study, treatment groups included E7449 (100 mg/kg) and E7389 (0.05 or 0.1 mg/kg) as single agents and 2 groups treated with the combination of E7449 and E7389. E7449 was orally administered once daily at 100 mg/kg for 28 days and E7389 was intravenously administered at 0.05 or 0.1 mg/kg once every 4 days, 4 times. In the second study, treatment groups included E7449 (60 or 100 mg/kg) and carboplatin (15 or 60 mg/kg) as single agents and 3 groups treated with both agents in combination. E7449 was orally administered once daily at 60 or 100 mg/kg for 28 days and carboplatin was intravenously administered at 15 or 60 mg/kg once, on the first day of drug treatment. E7449 as a single agent lacked significant antitumor activity in this model. Dose-dependent antitumor activity was observed following treatment with E7389 alone at the 0.05 and 0.1 mg/kg doses. Combination with E7449 did not increase the antitumor activity of E7389. Modest antitumor activity was observed following treatment with carboplatin alone at the 15 and 60 mg/kg doses. Combination with E7449 (60 or 100 mg/kg) did not increase the antitumor activity of carboplatin. All drug treatments were well tolerated without any deaths or significant body weight loss.

Objective

The purpose of this study was to investigate the combination activity of E7449 treatment with E7389 or carboplatin on the growth of subcutaneously implanted MDA-MB-231 human breast cancer cells in athymic mice.

Materials and Methods

The vehicle for E7449 was 0.5% methyl cellulose. E7449 powder was ground using a mortar and pestle. Vehicle was gradually added and mixed with the compound to make a 10 mg/mL stock solution.

The stock solution was diluted with vehicle to a concentration of 6 mg/mL. Solutions were divided into aliquots and stored at 4° C. for up to 7 days.

The vehicle for E7389 was saline (0.9% sodium chloride). E7389 stock solution (0.5 mg/mL) was diluted with vehicle to concentrations of 0.01 and 0.005 mg/mL. E7389 was formulated fresh on each day of treatment.

The vehicle for carboplatin was saline (0.9% sodium chloride). Carboplatin powder (50 mg) was dissolved in 8.33 mL saline to make a stock solution of 6 mg/mL. Stock solution was diluted with vehicle to a concentration of 1.5 mg/mL. Carboplatin was formulated fresh on the day of treatment.

The cells used were human breast cancer cells MDA-MB-231 (ATCC® HTB-26™), American Type Culture Collection (ATCC), Manassas, Va.

The mice used were female, 6 week old, CrTac:NCr-Foxn1$^{nu}$, Taconic, Hudson, N.Y.

Measurement of Antitumor Activity

MDA-MB-231 human triple negative breast cancer cells are wild type for BRCA1 and 2 and PTEN. Cells were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and resuspended in ice-cold PBS. Female immunodeficient athymic mice were inoculated subcutaneously near the right axillary area with MDA-MB-231 cells ($5 \times 10^6$) in a 1:1 ratio (50 μL each) with Matrigel™ in a volume of 0.1 mL in phosphate buffered saline, using a 26-gauge needle. A total of 94 mice, approximately 6 weeks old were implanted with MDA-MB-231 cells.

E7449, carboplatin and E7389 were evaluated as single agents and in combination for antitumor activity against MDA-MB-231 human breast cancer xenografts in athymic mice. The first experiment consisted of a vehicle control group, an E7449 single agent group, 2 groups treated with single agent E7389 and 2 combination drug-treated groups (Table 5). Thirty-nine mice were inoculated with MDA-MB-231 cells and on Day 21 following implantation, tumor volumes were measured and mice were randomized into the 6 treatment groups based on tumor volume (average of 300 mm$^3$). Following randomization drug treatment was initiated. Each group was composed of 5 mice for a total of 30 mice on the first day of treatment. E7449 was formulated in 0.5% methyl cellulose and orally administered once daily for 28 days at 100 mg/kg based on body weight at 0.1 mL per 10 g. E7389 was formulated in saline and was intravenously administered once every 4 days, 4 times (Day 21, 25, 29, and 33) at a dosage of 0.05 or 0.1 mg/kg as single agent or in combination with E7449, based on body weight at 0.1 mL per 10 g. The control group was treated with oral vehicle (0.5% methyl cellulose in water) daily and intravenous vehicle (saline) once every 4 days, 4 times. E7449 or vehicle was administered first and when dosing of all animals was complete E7389 was administered to animals receiving the combination.

TABLE 5

Treatment Groups for Investigation of Effect of E7449 and E7389 Alone and in Combination in MDA-MB-231 Human Breast Cancer Xenografts in Athymic Mice

| Group Number | Treatment | Route | Schedule | No. of Animals |
|---|---|---|---|---|
| A | Vehicle (0.5% methyl cellulose) + Vehicle (saline) | PO + IV | QDx28, Q4Dx4 | 5 |
| B | E7449 100 mg/kg | PO | QDx28 | 5 |
| C | E7389 0.1 mg/kg | IV | Q4Dx4 | 5 |
| D | E7389 0.05 mg/kg | IV | Q4Dx4 | 5 |
| E | E7449 100 mg/kg + E7389 0.1 mg/kg | PO + IV | QDx28, Q4Dx4 | 5 |
| F | E7449 100 mg/kg + E7389 0.05 mg/kg | PO + IV | QDx28, Q4Dx4 | 5 |

The second experiment consisted of a vehicle control group, 2 groups treated with single agent E7449, 2 groups treated with single agent carboplatin and 3 combination drug-treated groups (Table 6). Fifty five mice were inoculated with MDA-MB-231 cells and on Day 18 following implantation, tumor volumes were measured and mice were randomized into 8 treatment groups based on tumor volume (average of 300 mm$^3$). Following randomization drug treatment was initiated. Each group consisted of 5 mice for a total of 40 mice on the first day of treatment. E7449, formulated in 0.5% methyl cellulose was orally administered daily for 28 days, at 60 or 100 mg/kg based on body weight at 0.1 mL per 10 g. Carboplatin was formulated in saline and was intravenously administered once on the first day of treatment (Day 18) at a dosage of 15 or 60 mg/kg as a single agent or in combination with E7449 based on body weight at 0.1 mL per 10 g. The control group was treated with oral vehicle (0.5% methyl cellulose in water) daily and intravenous vehicle (saline) once on Day 18. E7449 or vehicle was administered first and when dosing of all animals was complete carboplatin was administered to animals receiving the combination.

TABLE 6

Treatment Groups for Investigation of Effect of E7449 and Carboplatin Alone and in Combination in MDA-MB-231 Human Breast Cancer Xenografts in Athymic Mice

| Group Number | Treatment | Route | Schedule | No. of Animals |
|---|---|---|---|---|
| A | Vehicle (0.5% methyl cellulose) + Vehicle (saline) | PO + IV | QDx28, QDx1 | 5 |
| B | E7449 100 mg/kg | PO | QDx28 | 5 |
| C | E7449 60 mg/kg | PO | QDx28 | 5 |
| D | Carboplatin 60 mg/kg | IV | QDx1 | 5 |
| E | E7449 100 mg/kg + Carboplatin 60 mg/kg | PO + IV | QDx28, QDx1 | 5 |
| F | E7449 60 mg/kg + Carboplatin 60 mg/kg | PO + IV | QDx28, QDx1 | 5 |
| G | Carboplatin 15 mg/kg | IV | QDx1 | 5 |
| H | E7449 100 mg/kg + Carboplatin 15 mg/kg | PO + IV | QDx28, QDx1 | 5 |

The general health of the mice was monitored and mortality recorded daily. Tumor volume was determined by caliper (Mitutoyo, Aurora, Ill.) measurements (mm) using the formula (l×w$^2$)/2=mm$^3$, where l and w refer to the larger and smaller perpendicular dimensions collected at each measurement. Tumor dimensions and body weights were recorded twice per week starting on the first day of treatment. Relative body weight was calculated as follows: Relative body weight=(body weight on day of measurement/body weight on first day of treatment). The data generated consist of group mean tumor volumes at each measurement and group mean body weights at each measurement. The mean±SEM for tumor volume and mean±SEM for relative body weight for each experimental group was calculated.

Drug treatment was initiated 21 or 18 days post tumor implantation, in the E7389 and carboplatin combination studies respectively, and continued for 28 days. Animals whose tumor measurement reached ≥2 cm at the longest axis or whose tumor became ulcerated were euthanized prior to study termination. The studies were terminated on Days 53 and 50 (E7389 and carboplatin combinations respectively). Statistical analyses were performed at vehicle endpoint for both studies (Day 42 for the E7389 combination and Day 39 for the carboplatin combination study).

Statistical Analysis

Figure 9:
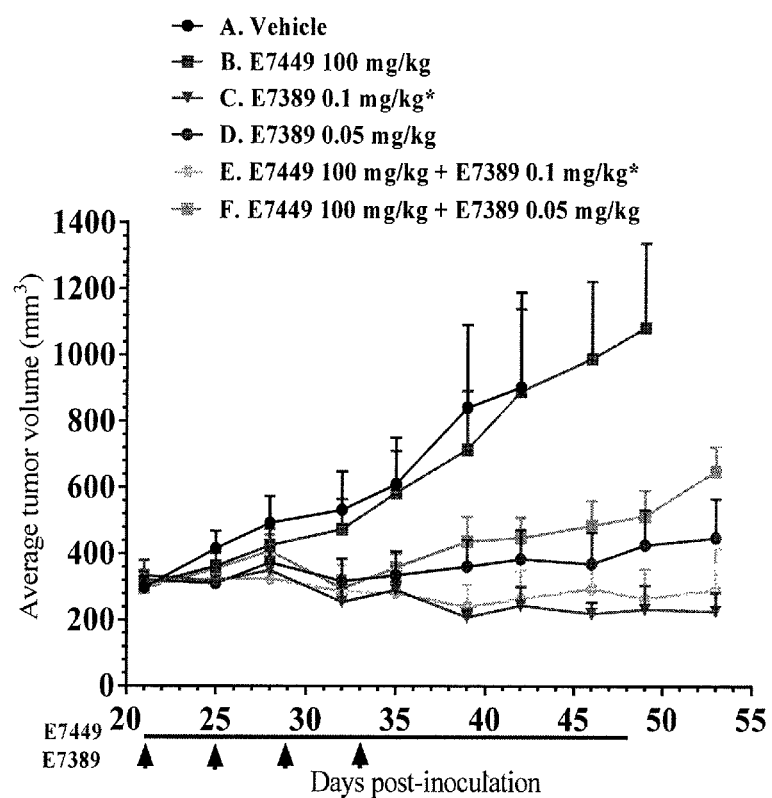
FIG. 9 is a graph showing an antitumor effect of E7449 and E7389 alone and in combination in MDA-MB-231 human breast cancer xenografts in athymic mice. Average tumor volume for the indicated treatment groups is shown as a function of time post inoculation.
Figure 10:
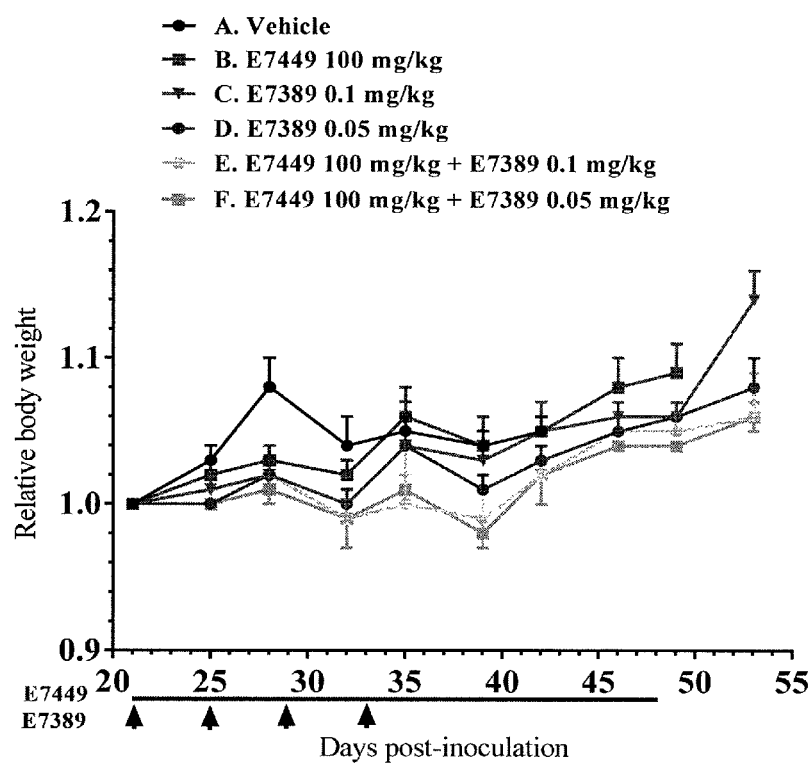
FIG. 10 is a graph showing relative body weights of mice treated with E7449 and E7389 alone and in combination in MDA-MB-231 human breast cancer xenografts in athymic mice. Relative body weight for the indicated treatment groups is shown as a function of time post inoculation.

Statistical analysis of vehicle groups versus all drug-treated groups was performed by a one way analysis of variance (ANOVA) for tumor volume followed by Dunnett's multiple comparisons test. The analyses were performed at vehicle endpoint for both studies (Day 42 for E7389 and Day 39 for the carboplatin combination study). A value of P<0.05 was considered statistically significant under a two-sided hypothesis. All statistical analyses were performed using GraphPad Prism 6 software (Lake Forest, Calif.).
Results
FIG. 9 shows the effect of E7449 and E7389 as single agents and in combination in MDA-MB-231 human breast cancer xenografts in athymic mice. Administration of single agent E7449 at 100 mg/kg did not significantly inhibit tumor growth. Dose dependent antitumor activity was observed with E7389 as single agent with a statistically significant effect observed only at the 0.1 mg/kg dose. E7449 in combination with E7389 at either dose had no impact on the antitumor activity of E7389 (FIG. 9). Administration of either drug as single agent or both drugs in combination had no significant effect on body weight (FIG. 10).

Data represent the mean±SEM. Final tumor volume measurements were reported for mice in groups receiving vehicle and E7449 alone (groups A and B) on Day 42 and 49: mice were then euthanized because of large or ulcerated tumors. Drug treatment stopped on Day 48 and the study was terminated on Day 53. No antitumor activity was observed for E7449 alone. Statistically significant inhibition of tumor growth was observed for E7389 at the 0.1 mg/kg dose as single agent and in combination (groups C and E): *$P<0.05$ versus vehicle on Day 42 (one-way ANOVA followed by Dunnett's multiple comparisons test). No difference was observed in antitumor activity of E7389 when combined with E7449.

Data show the mean±SEM. Final body weight measurements were reported for mice treated with vehicle and E7449 alone (groups A and B) on Day 42 and 49: mice were then euthanized because of large or ulcerated tumors. Drug treatment stopped on Day 48 and the study was terminated on Day 53. No significant body weight loss was observed in any of the drug treatment groups over the course of the study.

Figure 11:
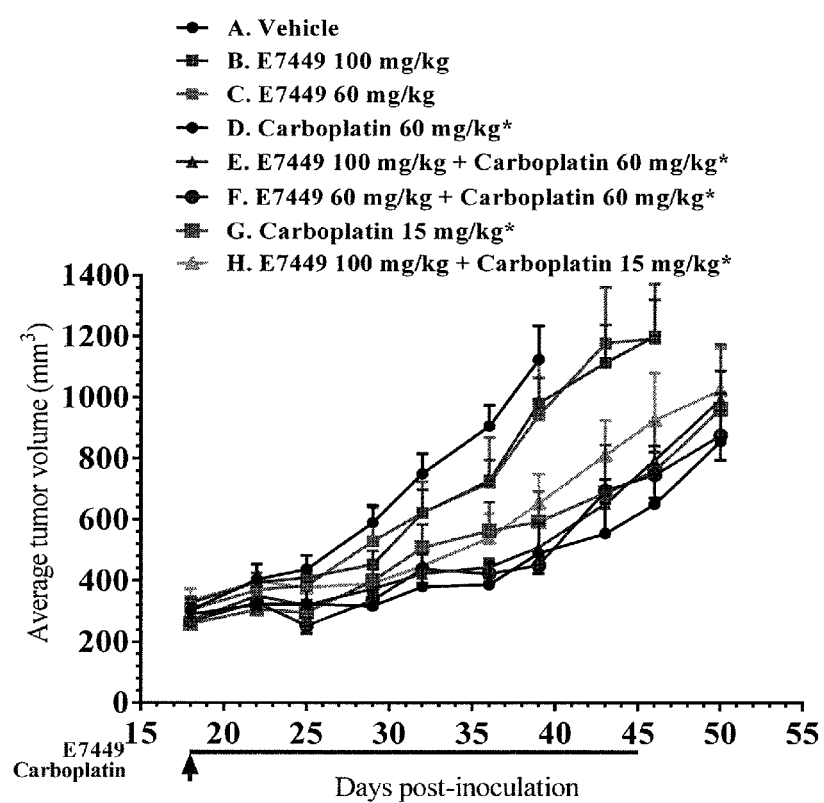
FIG. 11 is a graph showing an antitumor effect of E7449 and carboplatin alone and in combination in MDA-MB-231 human breast cancer xenografts in athymic mice. Average tumor volume for the indicated treatment groups is shown as a function of time post inoculation.
Figure 12:
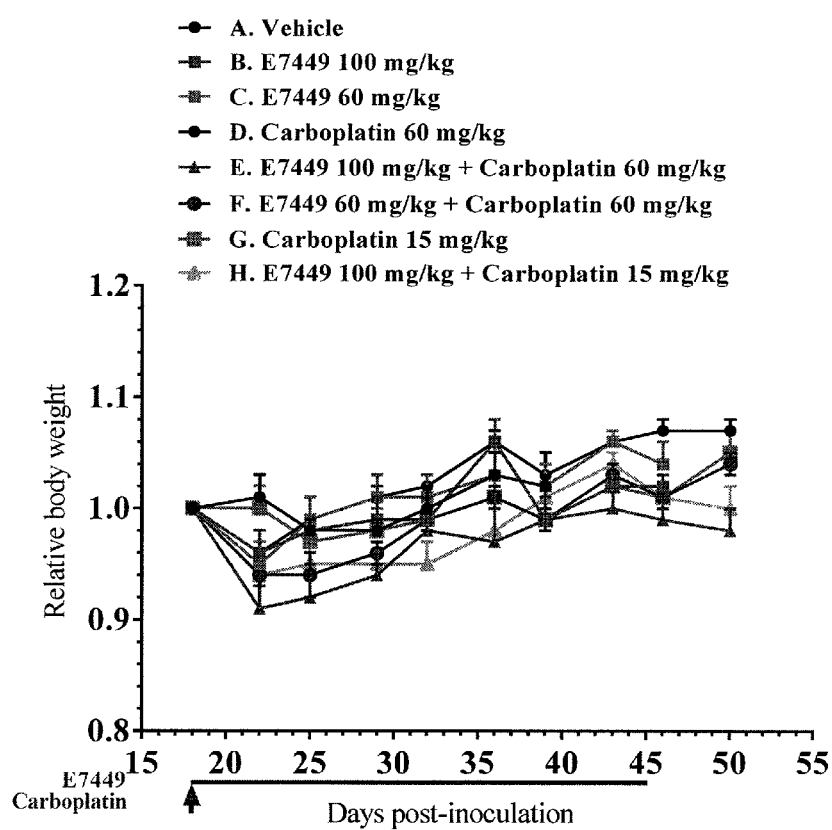
FIG. 12 is a graph showing relative body weights of mice treated with E7449 and carboplatin alone and in combination in MDA-MB-231 human breast cancer xenografts in athymic mice. Relative body weight for the indicated treatment groups is shown as a function of time post inoculation.

FIG. 11 shows the effect of E7449 and carboplatin as single agents and in combination in MDA-MB-231 human breast cancer xenografts in athymic mice. Administration of single agent E7449 at 60 or 100 mg/kg did not significantly inhibit tumor growth. Modest antitumor activity was observed with carboplatin as single agent at both dosages (15 and 60 mg/kg). Addition of E7449 (60 or 100 mg/kg) to carboplatin at either dose did not impact the antitumor activity of carboplatin (FIG. 11). Administration of either drug as single agent or both drugs in combination had no significant effect on body weight (FIG. 12).

Data represent the mean±SEM. Final tumor volume measurements were reported for mice treated with vehicle on Day 39 and for mice treated with E7449 alone (60 and 100 mg/kg) (groups B and C) on Day 46; mice were then euthanized because of large or ulcerated tumors. Drug treatment stopped on Day 45 and the study was terminated on Day 50. No antitumor activity was observed for E7449 alone. Statistically significant inhibition of tumor growth was observed for all other treatment groups: *$P<0.05$ versus vehicle on Day 39 (one-way ANOVA followed by Dunnett's multiple comparisons test). No difference was observed in antitumor activity of carboplatin when combined with E7449.

Data show the mean±SEM. Final body weight measurements were reported for mice treated with vehicle on Day 39 and for mice treated with E7449 alone (60 and 100 mg/kg) (groups B and C) on Day 46; mice were then euthanized because of large or ulcerated tumors. Drug treatment stopped on Day 45 and the study was terminated on Day 50. No significant body weight loss was observed in any of the drug treatment groups over the course of the study.

Conclusion
E7449 did not demonstrate antitumor activity as a single agent following 28 day dosing at 60 or 100 mg/kg in the BRCA and PTEN wild type MDA-MB-231 human triple negative breast cancer xenograft model in athymic mice. Single agent E7389 at dosage level 0.1 mg/kg (Q4D×4) resulted in statistically significant anticancer activity. Combination with E7449 did not enhance the antitumor effect of E7389 in the MDA-MB-231 model. Single agent carboplatin at dosage levels of 15 and 60 mg/kg (QD×1) resulted in modest but statistically significant anticancer activity. Combination with E7449 did not enhance the antitumor effect of carboplatin in this model. No significant toxicity as indicated by body weight loss was observed for any of the drug treatments.

Example 4

Effect of E7449 in Combination with Eribulin Mesylate on Growth of Subcutaneous Human Breast Cancer HCC1806 Xenografts in Athymic Mice
Summary
The effect of E7449 in combination with E7389 (eribulin mesylate) was examined in a subcutaneous human breast cancer HCC1806 xenograft model in athymic mice. Treatment groups included E7449 (100 mg/kg) and E7389 (0.1 or 0.4 mg/kg) as single agents and 2 groups treated with the drug combinations. E7449 was orally administered at 100 mg/kg once daily for 28 days and E7389 was intravenously administered at 0.1 or 0.4 mg/kg once every 4 days, 4 times. E7449 as a single agent lacked antitumor activity in this model. Significant and dose-dependent tumor growth inhibition was observed for E7389 alone at the 0.1 and 0.4 mg/kg doses. Combination of E7449 and E7389 did not increase the antitumor activity of E7389. Combination treatments were well tolerated without any deaths or significant body weight loss.
Objective
The purpose of this study was to investigate the combination activity of treatment with E7449 and E7389 on the growth of subcutaneously implanted HCC1806 human breast cancer cells in athymic mice.
Materials and Methods
The vehicle for E7449 was 0.5% methyl cellulose. E7449 powder was ground using a mortar and pestle. Vehicle was gradually added and mixed with the compound to make a stock 10 mg/mL solution. The stock solution was divided into aliquots and stored at 4° C. for up to 7 days.

The vehicle for E7389 was saline (0.9% sodium chloride). E7389 stock solution (0.5 mg/mL) was diluted with vehicle to concentrations of 0.04 and 0.01 mg/mL. E7389 was formulated fresh on each day of treatment.

The cells used were human breast cancer cells, HCC1806 (ATCC® CRL-2335™), American Type Culture Collection (ATCC).

The mice used were female, 6 week old, Crl:NU-Foxn1$^{nu}$, Charles River Laboratories (Wilmington, Mass.).
Measurement of Antitumor Activity
HCC1806 human triple negative breast cancer cells, wild type for BRCA and PTEN, were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and resuspended in ice-cold PBS. Female immunodeficient athymic mice were inoculated subcutaneously near the right axillary area using a 26-gauge needle with HCC1806 cells ($2.5\times10^6$) in a 0.1 mL volume. A total of 60 mice, approximately 6 weeks old were implanted with cells.

E7449 and E7389 were evaluated as single agents and in combination for anti-tumor activity against HCC1806 human breast cancer xenografts in athymic mice. The experiment consisted of a vehicle-treated control group, an E7449 single agent-treated group, two groups treated with single agent E7389 and 2 combination drug-treated groups (Table 7). Each group was composed of 8 mice for a total of 48 mice on the first day of treatment. Sixty mice were inoculated with HCC1806 cells and on day 5 following implantation, tumor volumes were measured and mice were randomized into the 6 treatment groups based on tumor volume (average of 150 mm$^3$). Following randomization drug treatment was initiated (Day 5). E7449 was formulated in 0.5% methyl cellulose and orally administrated daily at 100 mg/kg based on body weight at 0.1 mL per 10 g. E7449 was administered once daily for 28 days (starting on Day 5) as a single agent or in combination with E7389. E7389 was formulated in saline and was administered intravenously once every 4 days 4 times (Day 5, 9, 13, and 17) at a dosage of 0.1 or 0.4 mg/kg as single agent or in combination with E7449, based on body weight at 0.1 mL per 10 g. The control group was treated with oral vehicle (0.5% methyl cellulose in water) daily and intravenous vehicle (saline) once every 4 days, 4 times. E7449 or vehicle was administered first and when dosing of all animals was complete E7389 was administered to animals receiving the combination.

The general health of the mice was monitored and mortality recorded daily. Tumor volume was determined by caliper (Mitutoyo, Aurora, Ill.) measurements (mm) using the formula $(I \times w^2)/2 = mm^3$, where I and w refer to the larger and smaller perpendicular dimensions collected at each measurement. Tumor dimensions were recorded twice per week starting at the initiation of drug treatment. Body weights were recorded twice per week starting on the first day of treatment. Relative body weight was calculated as follows: Relative body weight=(body weight on day of measurement/body weight on first day of treatment). The data generated consist of group mean tumor volumes and group mean body weights at each measurement. The mean±SEM for tumor volume and mean±SEM for relative body weight for each experimental group was calculated.

Drug treatment was initiated following randomization on Day 5 (5 days post tumor implantation) and continued for 28 days. Animals whose tumor measurement reached ≥2 cm at the longest axis were euthanized prior to study termination. The study was terminated on Day 38. Statistical analysis was performed on Day 20.

TABLE 7

Treatment Groups for Investigation of Effect of E7449 and E7389 Alone and in Combination in HCC1806 Human Breast Cancer Xenografts in Athymic Mice

| Group Number | Treatment | Route | Schedule | No. of Animals |
|---|---|---|---|---|
| A | Vehicle (0.5% methyl cellulose) + Vehicle (saline) | PO + IV | QDx28, Q4Dx4 | 8 |
| B | E7449 100 mg/kg | PO | QDx28 | 8 |
| C | E7389 0.4 mg/kg | IV | Q4Dx4 | 8 |
| D | E7389 0.1 mg/kg | IV | Q4Dx4 | 8 |
| E | E7449 100 mg/kg + E7389 0.4 mg/kg | PO + IV | QDx28, Q4Dx4 | 8 |
| F | E7449 100 mg/kg + E7389 0.1 mg/kg | PO + IV | QDx28, Q4Dx4 | 8 |

Statistical Analysis

Statistical analysis of the vehicle group (A) versus all drug treatment groups (B, C, D, E and F) was performed by a one way analysis of variance (ANOVA) for tumor volume followed by Dunnett's multiple comparison test. The analysis was performed on Day 20 of the study (vehicle endpoint). A value of P<0.05 was considered statistically significant under a two-sided hypothesis. All statistical analyses were performed using GraphPad Prism 6 software (Lake Forest, Calif.).

Results

Figure 13:
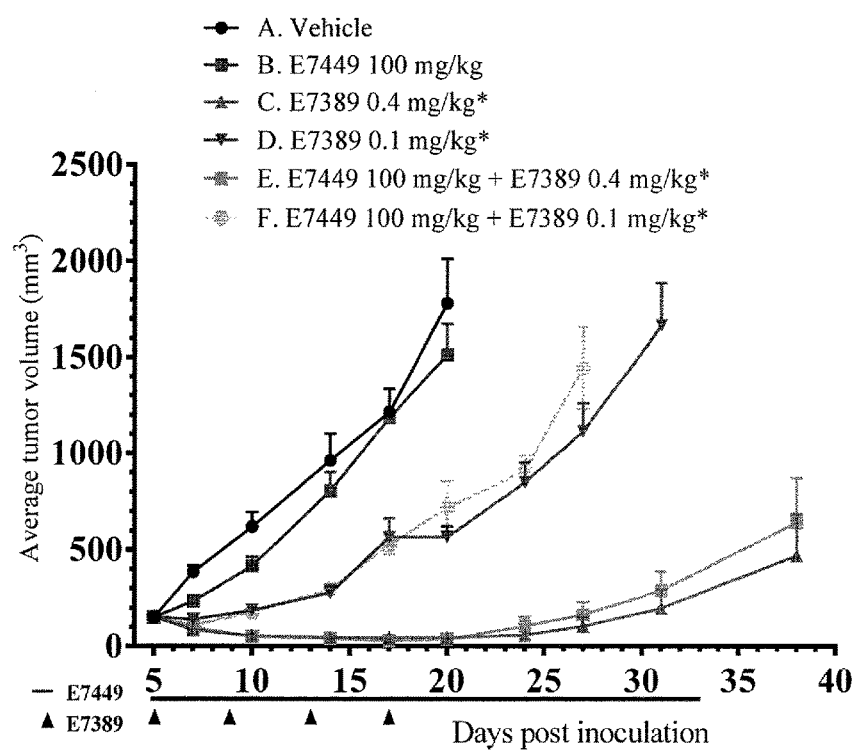
FIG. 13 is a graph showing an antitumor effect of E7449 and E7389 alone and in combination in HCC1806 human breast cancer xenografts in athymic mice. Average tumor volume for the indicated treatment groups is shown as a function of time post inoculation.
Figure 14:
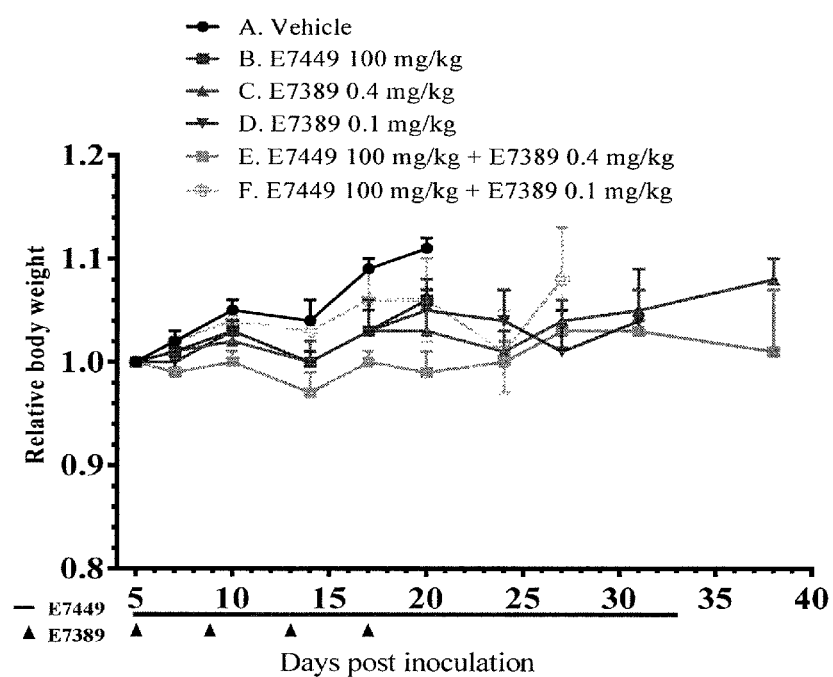
FIG. 14 is a graph showing relative body weights of mice treated with E7449 and E7389 alone and in combination in HCC1806 human breast cancer xenografts in athymic mice. Relative body weight for the indicated treatment groups is shown as a function of time post inoculation.

FIG. 13 shows the effect of E7449 and E7389 as single agents and in combination in HCC1806 human breast cancer xenografts in athymic mice. Single agent administration of E7449 at 100 mg/kg had no effect on tumor growth. Dose-dependent antitumor activity was observed with E7389 treatment: 0.1 mg/kg resulted in tumor growth inhibition and 0.4 mg/kg caused tumor regression. E7449 in combination with E7389 at either dose had no impact on the antitumor activity of E7389 (FIG. 13). Administration of either drug as single agent or both in combination had no significant effect on body weight (FIG. 14).

Data represent the mean±SEM. Mice in vehicle and E7449 alone groups (A and B) were euthanized on Day 20 because of large tumors. Final tumor measurements were recorded for mice in group B, receiving E7389 (0.1 mg/kg) alone and in combination (groups D and F) on Days 32 and 27 respectively; mice were then euthanized because of large tumors. Drug treatment stopped on Day 32 and the study was terminated on Day 38. No antitumor activity was observed for E7449 alone. Statistically significant inhibition of tumor growth observed for all other treatment groups: *P<0.0001 versus vehicle on Day 20 (one-way ANOVA followed by Dunnett's multiple comparison test). No difference was observed in antitumor activity of E7389 when combined with E7449.

Data show the mean±SEM. Mice in vehicle and E7449 alone groups (A and B) were euthanized on Day 20 because of large tumors. Final body weight measurements were recorded for E7389 (0.1 mg/kg) alone and in combination (groups D and F) on Days 32 and 27 respectively; mice were then euthanized because of large tumors. Drug treatment stopped on Day 32 and the study was terminated on Day 38. No significant body weight loss was observed in any of the drug treatment groups over the course of the study.

Conclusion

E7449 did not demonstrate antitumor activity as a single agent following 28 day dosing at 100 mg/kg in the BRCA and PTEN wild type HCC1806 human triple negative breast cancer xenograft model in athymic mice. Single agent E7389 at dosage levels of 0.1 and 0.4 mg/kg (Q4Dx4) resulted in statistically significant and dose-dependent anti-cancer activity. Combination with E7449 did not enhance the antitumor effect of E7389 in the HCC1806 model. No significant toxicity as indicated by body weight loss was observed for any of the drug treatments.

Example 5

Figure 15:
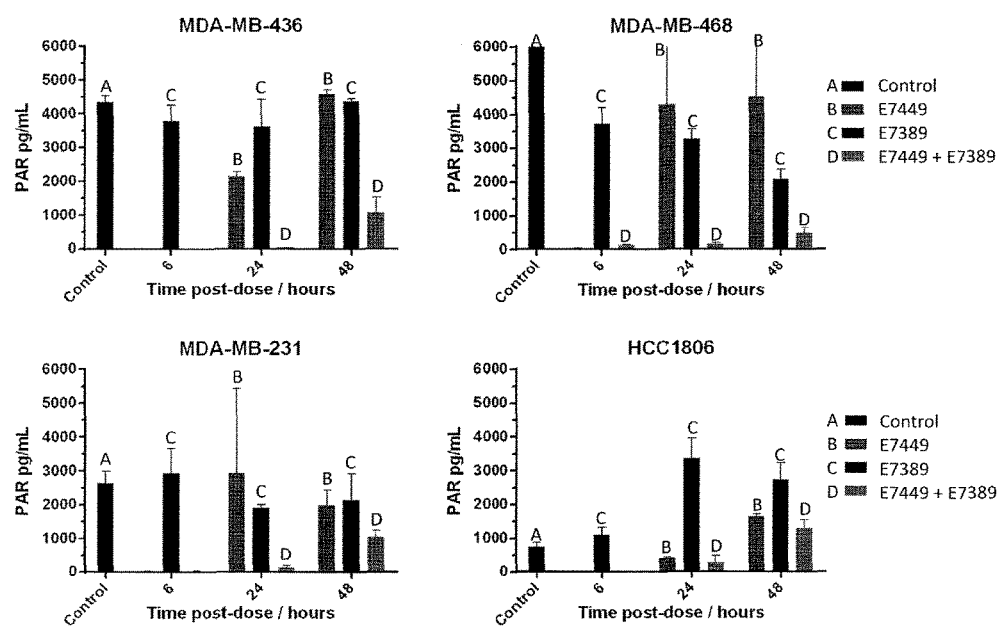
FIG. 15 is a set of graphs showing pharmacodynamic (PD) biomarker analysis of poly (ADP-ribose) (PAR) levels in triple negative breast cancer tumor lysates.

Pharmacodynamic (PD) Biomarker Analysis of Poly (ADP-Ribose) (PAR) Levels in Tumor Lysates FIG. 15 shows the effects of E7449 and E7389 as single agents and in combination on PAR levels in tumor lysates of four xenograft models of triple negative breast cancer (MDA-MB-436, MDA-MB-468, MDA-MB-231, and HCC1806). Significant differences were observed in basal PAR levels of the four tumor lysates. E7449 treatment resulted in complete PARP inhibition at 6 hours, and thus no PAR was detected in all four tumor lysates at this time point. PAR levels rebounded at 24 hours in all models. E7389 treatment alone did not inhibit PARP activity. E7449 and E7389 combination treatment resulted in sustained PAR inhibition in all models. PAR levels rebounded to various degrees at 48 hours in combination treatment. In the HCC1806 (wild type for BRCA and PTEN) tumor lysate, E7389 treatment alone increased PAR at 24 and 48 hours. PAR analysis in tumor lysates revealed a delayed rebound of PAR levels in E7449 and E7389 combination treated tumors versus E7449 alone.

Example 6

Pharmacodynamic (PD) Biomarker Analysis of Total Akt Levels in Tumor Lysates

Figure 16:
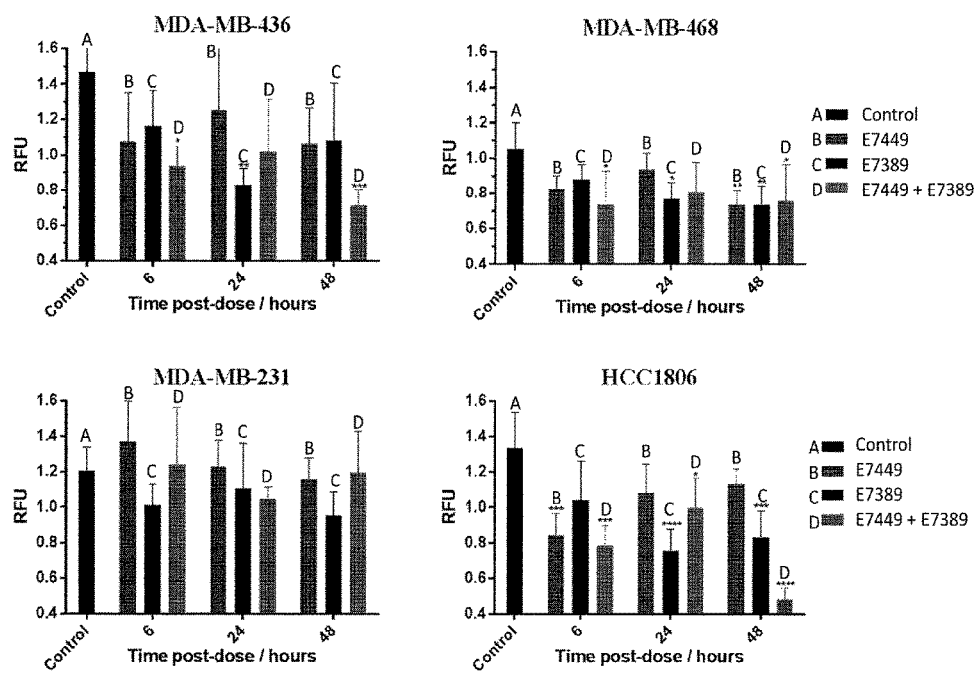
FIG. 16 is a set of graphs showing PD biomarker analysis of total Akt levels in triple negative breast cancer tumor lysates.

FIG. 16 shows the effects of E7449 and E7389 as single agents and in combination on total Akt levels in tumor lysates of four xenograft models of triple negative breast cancer (MDA-MB-436, MDA-MB-468, MDA-MB-231, and HCC1806). Multiple proteins in the P13K pathway were assessed by reverse phase protein microarray (RPMA) in tumor lysates. Akt levels decreased in all models except MDA-MB-231 (wild type for BRCA1 and 2 and PTEN) following single agent and combination treatments. This effect is specific for Akt as no changes in total PI3K, Erk, or Src were observed. Phosphorylated Akt (S473 & T308) decreased by E7389 and combination treatment at 48 hours in MDA-MB-468 tumors. Increased phosphorylated Akt (S473 & T308) and phosphorylated Erk (T202/Y204) following E7449 treatment were observed at early time points in HCC1806 tumors. No significant effects of treatment were observed on phosphorylated Src (Y527) levels in any tumor models. In summary, the most significant effect on P13K pathway proteins was a decrease in total Akt, which was observed in both sensitive and resistant tumor models.

Example 7

Figure 17:
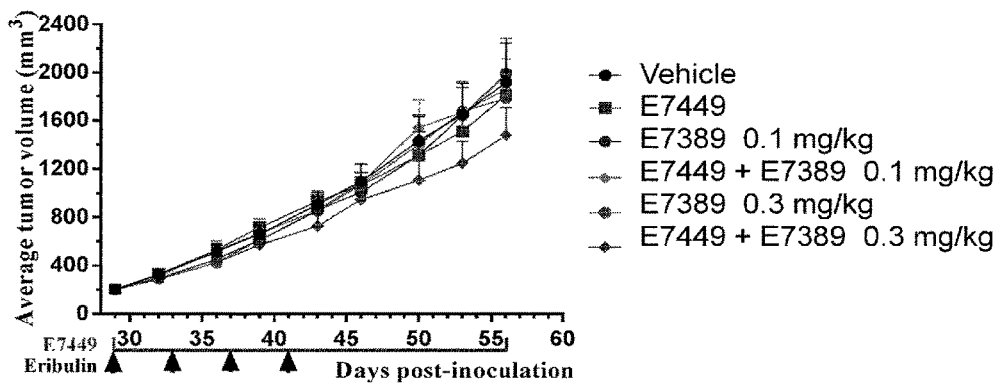
FIG. 17 is a set of graphs showing antitumor effects of E7449 and E7389 alone and in combination in patient-derived xenografts (PDx) in athymic mice. Average tumor volume for the indicated treatment groups is shown as a function of time post inoculation.
Figure 17:
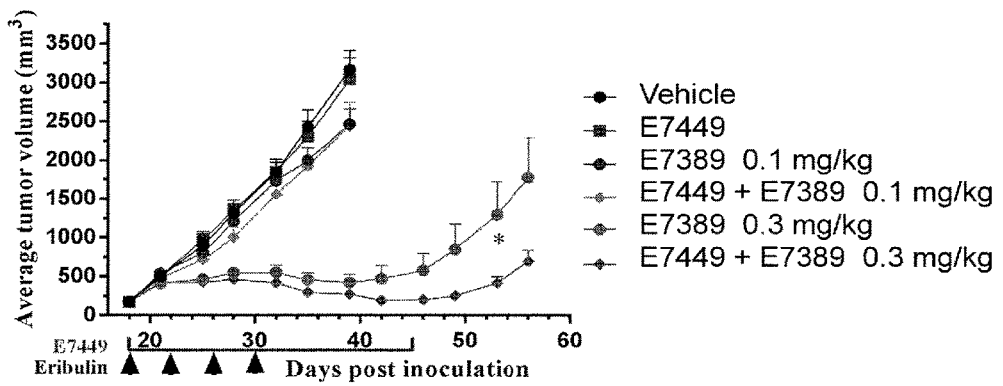
Figure 17:
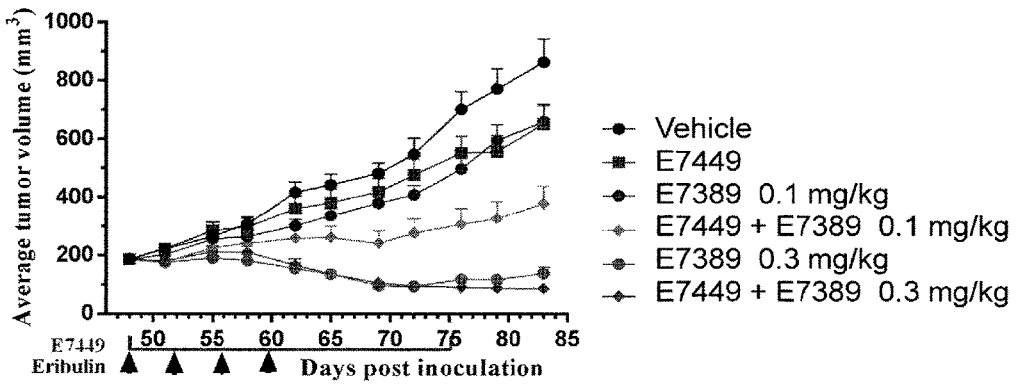

Effect of E7449 in Combination with E7389 on Growth of Patient-Derived Xenografts (PDx) of Triple Negative Breast Cancer FIG. 17 shows the effects of E7449 and E7389 as single agents and in combination in PDx models of triple negative breast cancer (BR1458, BR1282, and BR1474). BR1458 appeared to be resistant to single agent or combination treatment at administered doses. In BR1282, single agent administration of E7449 or E7389, as well as combination treatment at 0.1 mg/kg had no impact on the tumor growth. E7389 treatment at 0.3 mg/kg and combination of E7449 with E7389 at 0.3 mg/kg inhibited tumor growth to a similar degree, however, a statistically significant delayed time to progression of tumors was observed in mice treated with combination versus E7389 alone. In BR1474, E7389 treatment at 0.3 mg/kg and combination treatment with E7389 at 0.1 mg/kg and 0.3 mg/kg, had enhanced antitumor activity. All three PDx models were determined to be PTEN negative by immunohistochemistry (IHC). Furthermore, next generation sequencing (NGS) analysis revealed BRCA WT status for BR1458 and BR1282, whereas a deleterious BRCA1 mutation was detected in BR1474. BRCA status appeared to impact sensitivity to combination treatment. In the three PDx models, BR1474 was the most sensitive to E7449 as a single agent and E7449 and E7389 as a combination.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein.

All publications and patent applications mentioned in this specification are herein incorporated by reference to the same extent as if each independent publication or patent application was specifically and individually indicated as being incorporated by reference in their entirety.

Use of singular forms herein, such as "a" and "the," does not exclude indication of the corresponding plural form, unless the context indicates to the contrary. Similarly, use of plural terms does not exclude indication of a corresponding singular form.

The invention is further described in the following numbered paragraphs.

1. A method for treating a subject having or at risk of developing cancer, the method comprising administering to the subject (i) eribulin or a pharmaceutically acceptable salt thereof, and (ii) a poly (ADP-ribose) polymerase (PARP) inhibitor, or a pharmaceutically acceptable salt, hydrate, solvate, or amorphous solid thereof.

2. The method of paragraph 1, wherein the cancer is homologous recombination (HR)-deficient.

3. The method of paragraph 2, wherein said HR-deficient cancer is BRCA1, BRCA2, PTEN, ATM, MRE11, PALB2, RAD54, RAD54B, RAD50, RAD51, RAD51B, RAD51C, RAD51D, DMC1, XRCC2, SRCC3, RAD52, BRIP1, NBS1, WRN, BLM, Ku70, Ku80, ATR chk1, chk2, FANCA, FANCB, FANCC, FANCD1, FANCD2, FANCE, FANCF, FANCG, RAD1, RAD9, FEN-1, Mus81, Eme1, DDS1, BARD, XRCC1, ADPRT (PARP-1), ADPRTL2 (PARP-2), CTPS, RPA, RPA1, RPA2, RPA3, XPD, ERCC1, XPF, and/or MMS19 deficient.

4. The method of any one of paragraphs 1 to 3, wherein said subject is a human patient.

5. The method of any one of paragraphs 1 to 4, wherein said subject is diagnosed with a cancer, in treatment for cancer, or in post-therapy recovery from cancer.

6. The method of any one of paragraphs 1 to 5, wherein said cancer is a primary tumor.

7. The method of any one of paragraphs 1 to 5, wherein said cancer is a metastasis.

8. The method of any one of paragraphs 1 to 7, wherein said cancer is a solid tumor.

9. The method of any one of paragraphs 1 to 8, wherein said cancer is selected from the group consisting of breast cancer (e.g., estrogen receptor positive or negative, progesterone receptor positive or negative, HER-2 positive or negative, triple-negative breast cancer, or BRCA1 and/or BRCA2 positive or negative), lung cancer (e.g., non-small cell lung cancer and small cell lung cancer), ovarian cancer, endometrial cancer, prostate cancer, pharyngeal cancer, esophageal cancer, glioblastoma, adrenal cancer, B-cell malignancies, biliary tract cancer, bladder cancer, bone cancer, brain cancer, cervical cancer, choriocarcinoma, colon cancer, colorectal cancer, connective tissue cancer, cancer of the digestive system, gallbladder cancer, gastric cancer, cancer of the head and neck, hepatocellular carcinoma, intra-epithelial neoplasm, kidney cancer, liver cancer, lymphoma, skin cancer (e.g., melanoma and basal cell carcinoma), neuroblastoma, mesothelioma, neuroglioma, oral cavity cancer, pediatric cancer, pancreatic cancer, pancreatic endocrine tumors, pituitary adenoma, thymoma, renal cell carcinoma, cancer of the respiratory system, salivary gland cancer, sarcoma (e.g., Ewing's sarcoma, fibrosarcoma, and rhabdomyosarcoma), small bowel cancer, testicular cancer, thyroid cancer, ureteral cancer, cancer of the urinary system, and hematological cancers (e.g., acute myeloid leukemia and multiple myeloma).

10. The method of paragraph 9, wherein said cancer is selected from breast cancer and lung cancer.

11. The method of any one of paragraphs 1 to 10, wherein said pharmaceutically acceptable salt of eribulin is eribulin mesylate.

12. The method of any one of paragraphs 1 to 11, wherein said eribulin or said pharmaceutically acceptable salt thereof is administered by intravenous infusion.

13. The method of paragraph 12, wherein said intravenous infusion is for about 1 to about 20 minutes, or about 2 to about 5 minutes.

14. The method of any one of paragraphs 1 to 13, wherein said eribulin or said pharmaceutically acceptable salt thereof is administered in an amount in the range of about 0.1 mg/m$^2$ to about 20 mg/m$^2$, or in an amount of about 0.7 mg/m$^2$, 1.1 mg/m$^2$, or 1.4 mg/m$^2$.

15. The method of any one of paragraphs 1 to 14, wherein said eribulin or said pharmaceutically acceptable salt thereof is administered once on each of days 1 and 8 of a 21-day cycle.

16. The method of any one of paragraphs 1 to 15, wherein said PARP inhibitor is selected from the group consisting of E7449, olaparib, niraparib, rucaparib, veliparib, and BMN 673, and pharmaceutically acceptable salts, hydrates, solvates, or amorphous solid thereof.

17. The method of paragraph 16, wherein said PARP inhibitor is E7449 or a pharmaceutically acceptable salt thereof.

18. The method of paragraph 17, wherein said pharmaceutically acceptable salt of E7449 is the L-tartrate salt.

19. The method of any one of paragraphs 16 to 18, wherein said E7449 or said pharmaceutically acceptable salt thereof is administered orally.

20. The method of any one of paragraphs 16 to 19, wherein said E7449 or said pharmaceutically acceptable salt thereof is administered in an amount in the range of about 100 mg to about 1000 mg, or in an amount of about 200, 400, 600, or 800 mg.

21. The method of any one of paragraphs 1 to 20, wherein said PARP inhibitor, or said pharmaceutically acceptable salt, hydrate, solvate, or amorphous solid thereof, is administered once daily during a 21-day cycle.

22. The method of any one of paragraphs 1 to 21, further comprising administration of a platinum-based antineoplastic drug.

23. The method of paragraph 22, wherein said platinum-based antineoplastic drug is selected from the group consisting of cisplatin, carboplatin, oxaliplatin, satraplatin, picoplatin, nedaplatin, triplatin, and lipolatin.

24. The method of paragraph 22 or 23, wherein said platinum-based antineoplastic drug is administered once during a 21-day cycle.

25. The method of any one of paragraphs 1 to 24, wherein said treating: (i) reduces the number of cancer cells; (ii) reduces tumor volume; (iii) increases tumor regression rate; (iv) reduces or slows cancer cell infiltration into peripheral organs; (v) reduces or slows tumor metastasis; (vi) reduces or inhibits tumor growth; (vii) prevents or delays occurrence and/or recurrence of the cancer and/or extends disease- or tumor-free survival time; (viii) increases overall survival time; (ix) reduces the frequency of treatment; and/or (x) relieves one or more of symptoms associated with the cancer.

26. A method for decreasing the size of a tumor in a subject, the method comprising administering to the subject (i) eribulin or a pharmaceutically acceptable salt thereof, and (ii) a PARP inhibitor or a pharmaceutically acceptable salt, hydrate, solvate, or amorphous solid thereof.

27. The method of paragraph 26, wherein the tumor comprises HR-deficient cancer cells.

28. The method of paragraph 26 or 27, wherein said PARP inhibitor is E7449 or a pharmaceutically acceptable salt thereof.

29. The method of paragraph 28, wherein said pharmaceutically acceptable salt of E7449 is the L-tartrate salt.

30. The method of any one of paragraphs 26 to 29, wherein said pharmaceutically acceptable salt of eribulin is eribulin mesylate.

31. The method of any one of paragraphs 26 to 30, further comprising administration of a platinum-based antineoplastic drug.

32. The method of any one of paragraphs 1 to 31, wherein the amount of said eribulin, or said pharmaceutically acceptable salt thereof, and/or the amount of said PARP inhibitor or said pharmaceutically acceptable salt, hydrate, solvate, or amorphous solid thereof, administered to said subject provides a synergistic effect greater than the sum of the individual effects.

33. The method of any one of paragraphs 22 to 31, wherein the amount of said eribulin, or said pharmaceutically acceptable salt thereof, the amount of said PARP inhibitor or said pharmaceutically acceptable salt, hydrate, solvate, or amorphous solid thereof, and/or the amount of said platinum-based antineoplastic drug administered to said subject provides a synergistic effect greater than the sum of the individual effects.

34. The method of any one of paragraphs 1 to 33, wherein said eribulin, or said pharmaceutically acceptable salt thereof, or said PARP inhibitor, or said pharmaceutically acceptable salt, hydrate, solvate, or amorphous solid thereof, are co-administered.

35. The method of any one of paragraphs 1 to 33, wherein said eribulin, or said pharmaceutically acceptable salt thereof, or said PARP inhibitor, or said pharmaceutically acceptable salt, hydrate, solvate, or amorphous solid thereof, are administered sequentially.

36. The method of paragraph 34 or 35, further comprising co-administration of a platinum-based antineoplastic drug with either or both of said eribulin, or said pharmaceutically acceptable salt thereof, or said PARP inhibitor, or said pharmaceutically acceptable salt, hydrate, solvate, or amorphous solid thereof, or further comprising sequential administration of a platinum-based antineoplastic drug relative to said eribulin, or said pharmaceutically acceptable salt thereof, or said PARP inhibitor, or said pharmaceutically acceptable salt, hydrate, solvate, or amorphous solid thereof.

37. A kit for use in treating cancer or decreasing tumor size, the kit comprising (i) eribulin or a pharmaceutically acceptable salt thereof, and (ii) a PARP inhibitor or a pharmaceutically acceptable salt, hydrate, solvate, or amorphous solid thereof.

38. The kit of paragraph 37, wherein said PARP inhibitor is E7449 or said pharmaceutically acceptable salt thereof.

39. The kit of paragraph 38, wherein said pharmaceutically acceptable salt of E7449 is the L-tartrate salt.

40. The kit of any one of paragraphs 37 to 39, wherein said pharmaceutically acceptable salt of eribulin is eribulin mesylate.

41. The kit of any one of paragraphs 37 to 40, wherein said kit further comprises a platinum-based antineoplastic drug.

42. The kit of paragraph 41, wherein said platinum-based antineoplastic drug is selected from the group consisting of cisplatin, carboplatin, oxaliplatin, satraplatin, picoplatin, nedaplatin, triplatin, and lipolatin.

Other embodiments are within the scope of the following claims.

What is claimed is:

1. A method for treating a subject having or at risk of developing breast cancer, the method comprising administering to the subject (i) eribulin or a pharmaceutically acceptable salt thereof, and (ii) a poly (ADP-ribose) polymerase (PARP) inhibitor, or a pharmaceutically acceptable salt, hydrate, solvate, or amorphous solid thereof.

2. The method of claim 1, wherein the breast cancer is homologous recombination (HR)-deficient.

3. The method of claim 2, wherein said HR-deficient breast cancer is BRCA1, BRCA2, PTEN, ATM, MRE11, PALB2, RAD54, RAD54B, RAD50, RAD51, RAD51B, RAD51C, RAD51D, DMC1, XRCC2, SRCC3, RAD52, BRIP1, NBS1, WRN, BLM, Ku70, Ku80, ATR chk1, chk2, FANCA, FANCB, FANCC, FANCD1, FANCD2, FANCE, FANCF, FANCG, RAD1, RAD9, FEN-1, Mus81, Eme1, DDS1, BARD, XRCC1, ADPRT (PARP-1), ADPRTL2 (PARP-2), CTPS, RPA, RPA1, RPA2, RPA3, XPD, ERCC1, XPF, and/or MMS19 deficient.

4. The method of claim 1, wherein said subject is a human patient.

5. The method of claim 1, wherein said subject is diagnosed with breast cancer, in treatment for breast cancer, or in post-therapy recovery from breast cancer.

6. The method of claim 1, wherein said breast cancer is selected from the group consisting of estrogen receptor positive or negative, progesterone receptor positive or negative, HER-2 positive or negative, triple-negative breast cancer, or BRCA1 and/or BRCA2 positive or negative breast cancer.

7. The method of claim 1, wherein said pharmaceutically acceptable salt of eribulin is eribulin mesylate.

8. The method of claim 1, wherein said eribulin or said pharmaceutically acceptable salt thereof is administered by intravenous infusion.

9. The method of claim 1, wherein said eribulin or said pharmaceutically acceptable salt thereof is administered in an amount in the range of about 0.1 mg/m$^2$ to about 20 mg/m$^2$, or in an amount of about 0.7 mg/m$^2$, 1.1 mg/m$^2$, or 1.4 mg/m$^2$.

10. The method of claim 1, wherein said eribulin or said pharmaceutically acceptable salt thereof is administered once on each of days 1 and 8 of a 21-day cycle.

11. The method of claim 1, wherein said PARP inhibitor is selected from the group consisting of E7449, olaparib, niraparib, rucaparib, veliparib, and BMN 673, and pharmaceutically acceptable salts, hydrates, solvates, or amorphous solid thereof.

12. The method of claim 11, wherein said PARP inhibitor is E7449 or a pharmaceutically acceptable salt thereof.

13. The method of claim 12, wherein said pharmaceutically acceptable salt of E7449 is the L-tartrate salt.

14. The method of claim 1, wherein said E7449 or said pharmaceutically acceptable salt thereof is administered orally.

15. The method of claim 1, wherein said E7449 or said pharmaceutically acceptable salt thereof is administered in an amount in the range of about 100 mg to about 1000 mg, or in an amount of about 200, 400, 600, or 800 mg.

16. The method of claim 1, wherein said PARP inhibitor, or said pharmaceutically acceptable salt, hydrate, solvate, or amorphous solid thereof, is administered once daily during a 21-day cycle.

17. The method of claim 16, wherein said platinum-based antineoplastic drug is selected from the group consisting of cisplatin, carboplatin, oxaliplatin, satraplatin, picoplatin, nedaplatin, triplatin, and lipolatin.

18. The method of claim 1, wherein said treating: (i) reduces the number of breast cancer cells; (ii) reduces breast cancer tumor volume; (iii) increases breast cancer tumor regression rate; (iv) reduces or slows breast cancer cell infiltration into peripheral organs; (v) reduces or slows breast cancer tumor metastasis; (vi) reduces or inhibits breast cancer tumor growth; (vii) prevents or delays occurrence and/or recurrence of the breast cancer and/or extends disease- or tumor-free survival time; (viii) increases overall survival time; (ix) reduces the frequency of treatment; and/or (x) relieves one or more of symptoms associated with the breast cancer.

19. A method for decreasing the size of a breast cancer tumor in a subject, the method comprising administering to the subject (i) eribulin or a pharmaceutically acceptable salt thereof, and (ii) a PARP inhibitor or a pharmaceutically acceptable salt, hydrate, solvate, or amorphous solid thereof.

20. The method of claim 19, wherein the tumor comprises HR-deficient cancer cells.

21. The method of claim 19, wherein said PARP inhibitor is E7449 or a pharmaceutically acceptable salt thereof.

22. The method of claim 21, wherein said pharmaceutically acceptable salt of E7449 is the L-tartrate salt.

23. The method of claim 19, wherein said pharmaceutically acceptable salt of eribulin is eribulin mesylate.

24. The method of claim 1, wherein the amount of said eribulin, or said pharmaceutically acceptable salt thereof, and/or the amount of said PARP inhibitor or said pharmaceutically acceptable salt, hydrate, solvate, or amorphous solid thereof, administered to said subject provides a synergistic effect greater than the sum of the individual effects.

25. The method of claim 1, wherein said eribulin, or said pharmaceutically acceptable salt thereof, or said PARP inhibitor, or said pharmaceutically acceptable salt, hydrate, solvate, or amorphous solid thereof, are co-administered.

26. The method of claim 1, wherein said eribulin, or said pharmaceutically acceptable salt thereof, or said PARP inhibitor, or said pharmaceutically acceptable salt, hydrate, solvate, or amorphous solid thereof, are administered sequentially.

27. The method of claim 25, further comprising co-administration of a platinum-based antineoplastic drug with either or both of said eribulin, or said pharmaceutically acceptable salt thereof, or said PARP inhibitor, or said pharmaceutically acceptable salt, hydrate, solvate, or amorphous solid thereof, or further comprising sequential administration of a platinum-based antineoplastic drug relative to said eribulin, or said pharmaceutically acceptable salt thereof, or said PARP inhibitor, or said pharmaceutically acceptable salt, hydrate, solvate, or amorphous solid thereof.

* * * * *

UNITED STATES PATENT AND TRADEMARK OFFICE
CERTIFICATE OF CORRECTION

PATENT NO. : 10,238,630 B2
APPLICATION NO. : 15/314200
DATED : March 26, 2019
INVENTOR(S) : David Cox et al.

Page 1 of 1

It is certified that error appears in the above-identified patent and that said Letters Patent is hereby corrected as shown below:

In the Specification

Column 16, Line 50, replace "E744830" with --É7449+--.

Column 19, Line 40, replace "Foxnr$^{u}$" with --*Foxn1$^{nu}$*--.

Column 20, Line 22, replace "Relative body weight=body" with --Relative body weight=(body--;
　　Line 30, replace "reached cm" with --reached ≥2cm--.

Column 29, Line 35, replace "P13K" with --PI3K--;
　　Line 48, replace "P13K" with --PI3K--.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*